United States Patent
Murayama

(10) Patent No.: US 8,979,918 B2
(45) Date of Patent: Mar. 17, 2015

(54) STENT, MICROCATHETER, BRAIDING APPARATUS FOR CONTINUOUS HOSELIKE BODY, AND PROCESS FOR MANUFACTURING STENT

(75) Inventor: Yuichi Murayama, Tokyo (JP)

(73) Assignee: Daisuke KAWABE, Osaka (JP)

( * ) Notice: Subject to any disclaimer, the term of this patent is extended or adjusted under 35 U.S.C. 154(b) by 1096 days.

(21) Appl. No.: 12/667,995

(22) PCT Filed: Jul. 4, 2008

(86) PCT No.: PCT/JP2008/062192
§ 371 (c)(1),
(2), (4) Date: Apr. 27, 2010

(87) PCT Pub. No.: WO2009/008373
PCT Pub. Date: Jan. 15, 2009

(65) Prior Publication Data
US 2010/0211154 A1 Aug. 19, 2010

(30) Foreign Application Priority Data

Jul. 6, 2007 (JP) ................................. 2007-178220
Apr. 22, 2008 (JP) ................................. 2008-111764

(51) Int. Cl.
*A61F 2/06* (2013.01)
*A61F 2/95* (2013.01)
(Continued)

(52) U.S. Cl.
CPC ... *A61F 2/95* (2013.01); *A61F 2/90* (2013.01); *A61F 2002/823* (2013.01); *A61F 2002/9522* (2013.01); *A61F 2250/0018* (2013.01); *A61F 2250/0017* (2013.01)
USPC ....................................................... 623/1.22

(58) Field of Classification Search
CPC ....... A61F 2/90; A61F 2/86; A61F 2002/823; A61F 2250/0017; A61F 2250/0023; A61F 2250/0028

USPC .............. 623/1.11, 1.15, 1.2, 1.22, 1.5, 1.51, 623/1.53, 1.54
See application file for complete search history.

(56) References Cited

U.S. PATENT DOCUMENTS 5,718,159 A 2/1998 Thompson
5,951,599 A 9/1999 McCrory
(Continued)

FOREIGN PATENT DOCUMENTS

EP 0775470 5/1997
EP 0880948 12/1998
(Continued)

OTHER PUBLICATIONS

Himeno, Ryutaro, "Bio-Mechanical Simulation at RIKEN, Current Status and its Future," Nagare, vol. 23, pp. 437-443 (2004).
(Continued)

*Primary Examiner* — Katherine Dowe
(74) *Attorney, Agent, or Firm* — Onello & Mello, LLP

(57) ABSTRACT

A stent (1) comprising a hoselike body obtained by braiding a multiplicity of thin wires (2) of superelastic metal into plaited form. In the longitudinal intermediate portion of the hoselike body, mutually neighboring individual thins wires (2) of superelastic metal are in contact with each other or close to each other with a minute interspace and are formed into a thin wire densely braided hose portion (3) with a length needed to block any opening of blood vessel dilation. At both side portions thereof, mutually neighboring individual thin wires (2) of superelastic metal are formed into a thin wire coarsely braided hose portion (4) provided with an interstice allowing passage of blood flow. The hoselike body when pulled in the longitudinal direction causes the individual thin wires (2) of superelastic metal to stretch into fine gathering, and when released from pulling can make resilient restoration to the original hoselike body.

5 Claims, 17 Drawing Sheets

(51) Int. Cl.
*A61F 2/90* (2013.01)
*A61F 2/82* (2013.01)

(56) References Cited

U.S. PATENT DOCUMENTS

| | | |
|---|---|---|
| 6,059,822 A | 5/2000 | Kanesaka et al. |
| 6,585,758 B1 | 7/2003 | Chouinard et al. |
| 7,160,319 B2 | 1/2007 | Chouinard et al. |
| 2003/0149473 A1 | 8/2003 | Chouinard et al. |
| 2004/0098099 A1 | 5/2004 | McCullach et al. |
| 2005/0137680 A1* | 6/2005 | Ortiz et al. .................. 623/1.16 |
| 2005/0240261 A1* | 10/2005 | Rakos et al. .................. 623/1.51 |

FOREIGN PATENT DOCUMENTS

| | | |
|---|---|---|
| EP | 1251796 B1 | 12/2004 |
| JP | 3002976 B2 | 11/1999 |
| JP | 3119831 B2 | 10/2000 |
| JP | 2001-509412 A | 7/2001 |
| JP | 2002-535075 A | 10/2002 |
| JP | 2003-513748 A | 4/2003 |
| JP | 2005-342539 A | 12/2005 |
| JP | 2008-57079 A | 3/2008 |
| WO | 00/44308 A2 | 8/2000 |
| WO | 200511527 | 2/2005 |

OTHER PUBLICATIONS

International Search Report issued Sep. 16, 2008 in related International application No. PCT/JP2008/062192.
Search Report dated Nov. 28, 2014 issued in corresponding European Patent Application No. 08777907.0.

\* cited by examiner

FIG.28
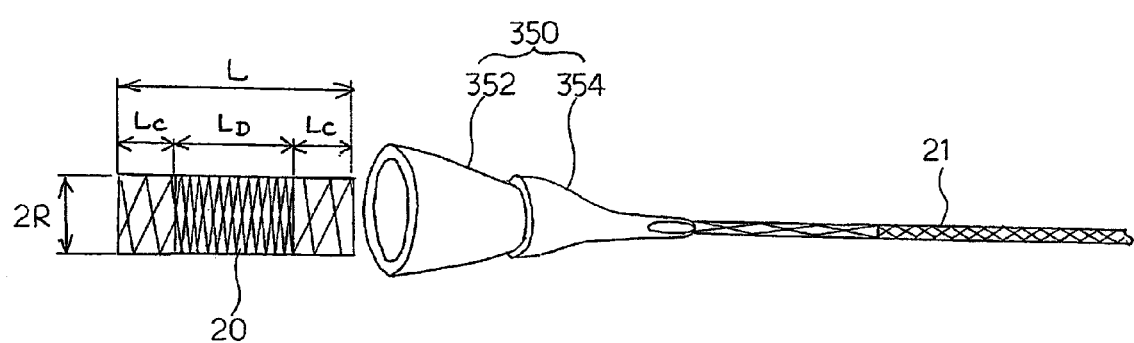
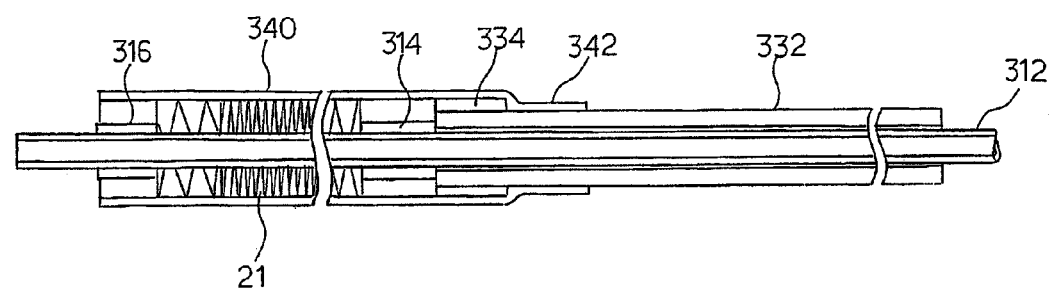
FIG.29

STENT, MICROCATHETER, BRAIDING APPARATUS FOR CONTINUOUS HOSELIKE BODY, AND PROCESS FOR MANUFACTURING STENT

TECHNICAL FIELD

The invention relates to a stent having a configuration that can be placed in a blood vessel and that is capable of closing at least part of an opening of a blood vessel dilation such as aneurysm and varix, blocking blood from flowing into the dilation, and thereby preventing the dilation from rupturing, a microcatheter for holding the stent, a continuous hoselike body braiding apparatus for forming the stent, and a process for manufacturing the stent.

BACKGROUND ART

For treatment against blood vessel dilation that is a disease of the artery or vein, as described in Non-Patent Document 1, there have been known a coil inserted into the blood vessel dilation, a stent inserted into a main blood vessel having the blood vessel dilation, and the like that are used in combination with a catheter, a balloon and the like.

As such a type of stent, there has conventionally been known a stent having a multiplicity of thin wires of elastic metal braided into a hoselike body with small interspaces provided between the wires, the hoselike body causing the individual thin wires to finely gather when pulled in the longitudinal direction and performing resilient restoration to the original hoselike body when released from pulling.

The conventional stent, however, has a defect in that sufficient blocking of blood flow from the blood vessel into the dilation cannot be achieved because of small interspaces opening between the thin wires of the stent once the stent that has been gathered finely by the pull in the longitudinal direction is inserted into the catheter, guided into the blood vessel, and pushed out of an extremity of the catheter in an area of development of the dilation so as to cause resilient restoration to the original hoselike state until the restored stent is set in a position such that the opening of the dilation is closed.

A stent having a multiplicity of thin wires of elastic metal arranged closely and braided into a hoselike body for improvement of blocking blood flow into the dilation has had a drawback of being prone to closing collateral vessels in the vicinity of a dilation even though it may be capable of blocking blood flow into the dilation when being guided likewise to an area of development of the dilation in a blood vessel and set in a position such that an opening of the dilation may be closed.

There has been proposed a stent in which a multiplicity of thin wires of elastic metal braided into a hoselike body with interspaces provided between the wires and in which a flexible synthetic resin film is stuck in a cylindrical shape on a portion of the hose having a length required for closure of an opening of dilation, whereas bulkiness of the synthetic resin film may make it impossible to insert the conventional stent in a bunched state into a microcatheter for guidance of the stent into a blood vessel.

As an art relating to the invention, an apparatus for forming an interknitted cord is disclosed in Patent Document 1. A mechanism obtained from improvement of an apparatus for manufacturing a plaited cord is used therein as an apparatus for forming a cord to be a base to attach a wig or an extension to a human head. The apparatus as described therein has a plurality of carriers attached with a bobbin and a mechanism to drive the carriers in a figure-of-8-like zigzag traveling route and performs action of knitting threads and interknitting hair by operating the carriers in a condition of extending the threads from the bobbin towards the head.

[NON-PATENT DOCUMENT 1]: Ryutaro Himeno "Bio-Mechanical Simulation at RIKEN, Current Status and its Future" ("NAGARE", vol. 23, p 437-p 443 (2004))

[PATENT DOCUMENT 1]: JP 2008-57079 A

DISCLOSURE OF THE INVENTION

Problems to be Solved by the Invention

An object of the invention is to provide a stent having a configuration that is capable of sufficiently preventing blood from flowing into a blood vessel dilation with little fear of closure of collateral vessels, and that can easily be inserted and guided into a microcatheter. Another object of the invention is to provide a microcatheter for holding such a stent. Another object of the invention is to provide a continuous hoselike body braiding apparatus for forming the stent. Another object of the invention is to provide a process for manufacturing the stent. Means that will be described below contribute to at least one of the objects.

Means for Solving the Problems

The invention proposes a stent comprising a hoselike body braided like knitting from a multiplicity of thin wires of superelastic metal, with a longitudinally intermediate portion of the hoselike body formed into a thin wire densely braided hose portion in which mutually neighboring superelastic metal thin wires are in contact with each other or close to each other with a minute interspace and which has a length required for closure of an opening of a blood vessel dilation, with both side portions thereof formed into thin wire coarsely braided hose portions in which mutually neighboring superelastic metal thin wires are provided with an interstice allowing passage of blood flow, the hoselike body having a configuration capable of causing the individual superelastic metal thin wires to extend and finely gather when pulled in a longitudinal direction and allowing resilient restoration to the original hoselike body when released from pulling.

A stent according to the invention is a stent in which a plurality of thin wires composed of shape memory material are intersected with each other and are braided into a hoselike body in a longitudinal direction with formation of reticulated gaps in the shape of diamond, the stent having thin wire coarsely braided hose portions in which the reticulated gaps having large opening areas are formed with coarse braiding along the longitudinal direction of the hoselike body, and a thin wire densely braided hose portion in which the reticulated gaps having smaller opening areas are formed with denser braiding than the thin wire coarsely braided hose portions along the longitudinal direction of the hoselike body, the stent characterized in that the narrower of intervals of two intersecting axes in the diamond-shaped reticulated gaps of the thin wire densely braided hose portion is not larger than 0.1 mm.

A stent according to the invention is a stent in which a plurality of thin wires composed of shape memory material are intersected with each other and are braided into a hoselike body in a longitudinal direction with formation of reticulated gaps in the shape of a diamond, the stent having thin wire coarsely braided hose portions in which the reticulated gaps having large opening areas are formed with coarse braiding along the longitudinal direction of the hoselike body, and a thin wire densely braided hose portion in which the reticulated gaps having smaller opening areas are formed with denser braiding than the thin wire coarsely braided hose portions along the longitudinal direction of the hoselike body, the thin wire densely braided hose portion being placed in an intermediate position excluding end portions of an overall length L of the hoselike body in the longitudinal direction, having a length along the longitudinal direction of the hoselike body in a range from one-quarter to one-tenth of the length L, and having the reticulated gaps with the narrower of intervals of two intersecting axes in the diamond-shaped reticulated gaps of not larger than 0.1 mm, the thin wire coarsely braided hose portions being placed on both sides of the thin wire densely braided hose portion along the longitudinal direction of the hoselike body and having the reticulated gaps with the narrower of intervals of two intersecting axes in the diamond-shaped reticulated gaps being wider than a diameter of a catheter used for treatment of blood vessel dilation.

In the stent according to the invention, the thin wire coarsely braided hose portions preferably have the reticulated gaps with the narrower of the intervals of the two intersecting axes in the diamond-shaped reticulated gaps being not smaller than 0.6 mm.

The stent according to the invention preferably has thin wire densely braided end portions that are placed at both ends of the hoselike body in the longitudinal direction and that are braided with a denser manner than that for the thin wire coarsely braided hose portions.

A microcatheter according to the invention is that for holding a stent that has a plurality of thin wires composed of shape memory material intersected with each other and braided into a hoselike body in a longitudinal direction with formation of reticulated gaps in the shape of diamonds, that has thin wire coarsely braided hose portions in which the reticulated gaps having large opening areas are formed with coarse braiding along the longitudinal direction of the hoselike body, that has a thin wire densely braided hose portion in which the reticulated gaps having smaller opening areas are formed with denser braiding than the thin wire coarsely braided hose portions along the longitudinal direction of the hoselike body, and that is provided with superelasticity, the microcatheter including: an inner catheter part having a wire insertion path in which a guide wire is inserted and a stent holding part which is provided on an outer circumference on extremity side thereof for holding the stent, and an outer sheath part that has a slide passage in which the inner catheter part is housed so as to be slidable in an axial direction, that withdraws and houses therein an extremity side of the inner catheter part with the stent stretched in the axial direction and held in the stent holding part in a return mode in which the inner catheter part is returned and slid to a front side, and that thrusts out the extremity side of the inner catheter part with the stent expanded to an original shape in radial directions in a push-in mode in which the inner catheter is pushed in and slid to the extremity side, the outer sheath part having a main body composed of a flexible tube and an extremity part which has a root part fixed to an extremity of the main body, which houses the stent holding part in the return mode, and which is formed of a heat-shrinkable film so as to have a predetermined outside diameter.

A continuous hoselike body braiding apparatus according to the invention has thin wire bobbins that are 2N in number and that are for supplying thin wires composed of shape memory material, a thin wire bobbin drive mechanism for causing right-handed revolution thin wire bobbins of N in number to make right-handed orbital motions about an axis of orbit at an orbital revolution velocity along one of two meandering paths provided around the axis of orbit and meandering with intersections, and for causing left-handed revolution thin wire bobbins of N in number to make left-handed orbital motions about the axis of orbit at the orbital revolution velocity along the other meandering path, a cylindrical winding shaft which has a diameter of 2R and around which the thin wires supplied from the thin wire bobbins numbering 2N are wound, a moving mechanism for moving the winding shaft in an axial direction, and a control unit for controlling the orbital revolution velocity of the thin wire bobbin drive mechanism and a moving velocity in the axial direction of the moving mechanism, winding thin wires numbering N from the right-handed revolution thin wire bobbins numbering N into a shape of right-handed helices around a cylindrical outer circumferential surface with a uniform right-handed winding pitch, winding thin wires numbering N from the left-handed revolution thin wire bobbins numbering N into a shape of left-handed helices around the cylindrical outer circumferential surface with a uniform left-handed winding pitch, making the right-handedly wound thin wires and the left-handedly wound thin wires undergo mutual oblique crossing like plain weave, and braiding a hoselike body having an inside diameter of 2R along the axial direction while forming diamond-shaped reticulated gaps, the control unit including coarsely braided hose portion forming means for forming thin wire coarsely braided hose portions, in which the reticulated gaps having large opening areas are formed with coarse braiding along the longitudinal direction of the hoselike body, on an outer circumference of the winding shaft with increase in a ratio of the moving velocity in the axial direction to the orbital revolution velocity, and thin wire densely braided hose portion forming means for forming a thin wire densely braided hose portion in which the reticulated gaps having smaller opening areas with denser braiding than the thin wire coarsely braided hose portions are formed along the longitudinal direction of the hoselike body, with decrease in the ratio of the moving velocity in the axial direction to the orbital revolution velocity.

A stent manufacturing process using a continuous hoselike body braiding apparatus having thin wire bobbins that are 2N in number and that are for supplying thin wires composed of shape memory material, a thin wire bobbin drive mechanism for causing right-handed revolution thin wire bobbins numbering N to make right-handed orbital motions about an axis of orbit at an orbital revolution velocity along one of two meandering paths provided around the axis of orbit and meandering with intersections, and for causing left-handed revolution thin wire bobbins numbering N to make left-handed orbital motions about the axis of orbit at the orbital revolution velocity along the other meandering path, and a moving mechanism for moving a winding shaft in an axial direction, the continuous hoselike body braiding apparatus for controlling the orbital revolution velocity of the thin wire bobbin drive mechanism and a moving velocity in the axial direction of the moving mechanism, winding thin wires numbering N from the right-handed revolution thin wire bobbins numbering N into a shape of right-handed helices around a cylindrical outer circumferential surface with a uniform right-handed winding pitch, winding thin wires numbering N from the left-handed revolution thin wire bobbins numbering N into a shape of left-handed helices around the cylindrical outer circumferential surface with a uniform left-handed winding pitch, making the right-handedly wound thin wires and the left-handedly wound thin wires undergo mutual oblique crossing like plain weave, and braiding a hoselike body having an inside diameter of 2R along the axial direction while forming diamond-shaped reticulated gaps, the stent manufacturing process comprising: a coarsely braided hose portion forming step for forming a thin wire coarsely braided hose portion in which reticulated gaps with large opening areas are formed with coarse braiding along the longitudinal direction of the hoselike body, with increase in a ratio of the moving velocity in the axial direction to the orbital revolution velocity, a thin wire densely braided hose portion forming step for forming a thin wire densely braided hose portion in which reticulated gaps having smaller opening areas with denser braiding than the thin wire coarsely braided hose portion are formed along the longitudinal direction of the hoselike body, with decrease in the ratio of the moving velocity in the axial direction to the orbital revolution velocity, a continuous hoselike body braiding step for braiding, around the winding shaft, the coarse-dense continuous hoselike body including at least one thin wire coarsely braided hose portion and at least one thin wire densely braided hose portion arranged in an order of predetermined lengths of the thin wire coarsely braided hose portion and the thin wire densely braided hose portion with an arrangement in a predetermined time series of high-velocity braiding periods in which the ratio of the moving velocity in the axial direction to the orbital revolution velocity is increased and the low-velocity braiding periods in which the ratio of the moving velocity in the axial direction to the orbital revolution velocity is decreased, a shape memory treatment step for removing the continuous hoselike body along with the winding shaft from the continuous hoselike body braiding apparatus and providing shape memory treatment thereto by heating to a temperature exceeding a transformation point of the thin wires composed of shape memory material, and a stent forming step for producing a stent provided with superelasticity by return temperatures of the continuous hoselike body and the winding shaft to normal and removal of the continuous hoselike body from the winding shaft.

Advantages of the Invention

According to the stent of the invention, pull in the longitudinal direction of the stent that is going to be inserted into the microcatheter causes the thin wires to extend and finely gather so as to facilitate the insertion into the microcatheter, and guidance of the stent in that state to an area of development of dilation in a blood vessel and setting of the stent on an opening of the dilation with extrusion thereof from the microcatheter cause the stent to resiliently restore to the original hoselike state, make the thin wire densely braided hose portion block the opening of the dilation, and thereby block blood flow into the dilation so as to prevent the dilation from rupturing, while closure of collateral vessels is avoided by previous designs of the length and the position for the setting of the thin wire densely braided hose portion and the like.

With at least one of the above configurations, the stent has the plurality of thin wires composed of shape memory material, intersected with each other, and braided into the hoselike body in the longitudinal direction with formation of the reticulated gaps in the shape of diamonds, and the stent has the thin wire coarsely braided hose portions in which the reticulated gaps having large opening areas are formed with coarse braiding and the thin wire densely braided hose portions in which the reticulated gaps having smaller opening areas are formed with denser braiding than the thin wire coarsely braided hose portions. The narrower of the intervals of the two intersecting axes in the diamond-shaped reticulated gaps of the thin wire densely braided hose portion is 0.1 mm or smaller.

In an observation of flow of fluid with stents having different reticulated gaps placed on a branching part in an obturator tube branching from a main fluid duct as modeled blood vessel dilation, the reticulated gap of zero, that is, tight contact between neighboring thin wires, prevents fluid from flowing into the obturator tube, as a matter of course. It was found that the fluid could not flow into the obturator tube on account of a property of the obturator tube under some conditions even though the reticulated gap was not zero. On a condition of an inside diameter of the tube of about 5 mm and a diameter of the thin wires forming the stent of about 50 μm, for instance, the narrower of the intervals of the two intersecting axes in the diamond-shaped reticulated gaps of 0.1 mm or smaller allows little fluid to flow into the obturator tube. The inside diameter of the tube of about 5 mm is in a range appropriate as an inside diameter of a blood vessel, the diameter of the thin wires of the stent of about 50 μm is in a range appropriate as that of proven material, and sizes of erythrocyte and leukocyte are known to be around 10 μm. It is therefore expected that inflow of blood into blood vessel dilation in a real blood vessel can effectively be blocked while manufacture of the stent is facilitated by avoidance of excessive density of the gap in the stent with the setting of the gap being 0.1 mm or smaller.

With at least one of the above configurations, the stent has the plurality of thin wires composed of shape memory material, intersected with each other, and braided into the hoselike body in the longitudinal direction with formation of the reticulated gaps in the shape of diamonds, and the stent has the thin wire coarsely braided hose portions in which the reticulated gaps having large opening areas are formed with coarse braiding and the thin wire densely braided hose portion in which the reticulated gaps having smaller opening areas are formed with denser braiding than the thin wire coarsely braided hose portions. The thin wire densely braided hose portion is placed in the intermediate position excluding end portions of the overall length L of the hoselike body in the longitudinal direction, has the length along the longitudinal direction of the hoselike body in the range from one-quarter to one-tenth of the length L, and has the reticulated gaps with the narrower of the intervals of the two intersecting axes in the diamond-shaped reticulated gapes of 0.1 mm or smaller. The thin wire coarsely braided hose portions are placed on both sides of the thin wire densely braided hose portion along the longitudinal direction of the hoselike body and have the reticulated gaps with the narrower of the intervals of the two intersecting axes in the diamond-shaped reticulated gaps being wider than a diameter of a catheter used for treatment of blood vessel dilation.

Blood flow into the blood vessel dilation does not occur through the whole opening that connects a main blood vessel and the blood vessel dilation, but may occur through part of the opening as in a manner of blood flow that enters into the blood vessel dilation through a downstream side of the opening, circulates in the dilation, and returns into the main blood vessel through an upstream side of the opening, for instance. In such a case, exertion of an excessive blood flow pressure on the blood vessel dilation can be suppressed by blocking of the blood flow in the inflow part or the outflow part. According to the above configuration, the thin wire densely braided hose portion having the length in the range from one-quarter to one-tenth of the overall length L of the hoselike body is placed in the intermediate position of the stent. Considering that the stent with the overall length L being about two times a length D of the opening of the blood vessel dilation is placed in the blood vessel, for instance, the length LD of the thin wire densely braided hose portion is within a range from D/2 to D/5. Even if the overall length L of the stent deviates from the value 2D, in the above configuration, the length of the thin wire densely braided hose portion can be a portion of the length D of the opening of the blood vessel dilation. The thin wire densely braided hose portion effectively blocks flow of the fluid as described above because the narrower of the intervals of the two intersecting axes in the diamond-shaped reticulated gaps is 0.1 mm or smaller.

The thin wire coarsely braided hose portions are placed on both sides of the thin wire densely braided hose portion, so that a portion of the opening of the blood vessel dilation can be covered with the thin wire densely braided hose portion with the remaining portion covered with the thin wire coarsely braided hose portions in the above configuration. The narrower of the intervals of the two intersecting axes in the diamond-shaped reticulated gaps of the thin wire densely braided hose portion is wider than a diameter of a catheter used for treatment of blood vessel dilation, so that the catheter can be made to pierce from inside of the stent through one of the reticulated gaps to the outside of the stent, if necessary. Such use of the stent makes it possible to insert the catheter for treatment from inside of the stent into the blood vessel dilation, for instance. With use of the catheter, the coil for insertion can be made to pierce from inside of the stent through the reticulated gap to the outside of the stent. Such use of the stent makes it possible to make the insertion coil from inside of the stent be implanted in the blood vessel dilation, for instance. The setting of the narrower of the intervals not less than 0.6 mm allows the microcatheter for treatment for common use to pierce the reticulated gaps.

The stent may further have the thin wire densely braided end portions that are placed at both ends of the hoselike body in the longitudinal direction and that are braided in a denser manner than that for the thin wire coarsely braided hose portions. The thin wire densely braided end portions, braided in the denser manner than the thin wire coarsely braided hose portion, resist raveling of the thin wires. When a stent is inserted into a blood vessel, the stent may detachably and attachably be held on an extremity of a guide wire, for instance, and the arrangement can improve reliability of the attachment and detachment.

The microcatheter is intended for holding the coarse-dense stent provided with superelasticity, and includes the inner catheter part having the wire insertion path in which the guide wire is inserted, and the stent holding part for holding the stent, and the outer sheath part having the slide passage in which the inner catheter part is housed. When the inner catheter part is returned to front side, the extremity side of the inner catheter part is withdrawn and housed therein with the stent stretched in the axial direction and held on the stent holding part. When the inner catheter is thrust out to the extremity side, the stent is released from the outer sheath part and is expanded in the radial directions so as to have the original shape. Thus the inner catheter part can be withdrawn so that the stent is stretched in the axial direction and is housed inside, and the inner catheter can be thrust out in a desired position in an artery, for instance, so that the stent is expanded to the original shape.

The outer sheath part of the microcatheter has a main body that is composed of a flexible tube and an extremity part that is formed of the heat-shrinkable film so as to have the predetermined outside diameter, and thus makes it possible to provide a small-size microcatheter having a thin extremity part, in particular, in comparison with microcatheters formed by common molding techniques.

The continuous hoselike body braiding apparatus braids the hoselike body by causing the right-handed revolution thin wire bobbins numbering N to make the right-handed orbital motions about the axis of orbit at the orbital revolution velocity along one of two meandering paths provided around the axis of orbit and meandering with intersections, causing the left-handed revolution thin wire bobbins numbering N to make the left-handed orbital motions about the axis of orbit at the orbital revolution velocity along the other meandering path, winding the thin wires supplied from the thin wire bobbins numbering 2N around the cylindrical winding shaft, and moving the winding shaft in the axial direction thereof. With the increase in the ratio of the moving velocity in the axial direction to the orbital revolution velocity, the thin wire coarsely braided hose portion in which the reticulated gaps having the large opening area with coarse braiding are formed along the longitudinal direction of the hoselike body is formed on the outer circumference of the winding shaft and, with the decrease in the ratio of the moving velocity in the axial direction to the orbital revolution velocity, the thin wire densely braided hose portion in which the reticulated gaps having the smaller opening area with denser braiding than the thin wire coarsely braided hose portions are formed along the longitudinal direction of the hoselike body is formed. By such change in the ratio of the moving velocity in the axial direction to the orbital revolution velocity, in this manner, the coarsely and densely continuous hoselike body that is to form the stent can be braided.

The stent manufacturing process includes: using the continuous hoselike body braiding apparatus that braids the hoselike body by causing the right-handed revolution thin wire bobbins numbering N to make the right-handed orbital motions about the axis of orbit at the orbital revolution velocity along one of two meandering paths provided around the axis of orbit and meandering with intersections, causing the left-handed revolution thin wire bobbins numbering N to make the left-handed orbital motions about the axis of orbit at the orbital revolution velocity along the other meandering path, winding the thin wires supplied from the thin wire bobbins numbering 2N around the cylindrical winding shaft, and moving the winding shaft in the axial direction thereof; braiding the coarsely and densely continuous hoselike body around the winding shaft by the arrangement in the predetermined time series of the high-velocity braiding periods in which the ratio of the moving velocity in the axial direction to the orbital revolution velocity is increased and the low-velocity braiding periods in which the ratio of the moving velocity in the axial direction to the orbital revolution velocity is decreased; removing the continuous hoselike body along with the winding shaft from the continuous hoselike body braiding apparatus; providing shape memory treatment by heating to a temperature exceeding the transformation point of the thin wires composed of shape memory material; and producing the stent provided with superelasticity by the return of the temperatures of the continuous hoselike body and the winding shaft to normal and the removal of the continuous hoselike body from the winding shaft. Thus the coarsely and densely continuous hoselike body can be braided by such change in the ratio of the moving velocity in the axial direction to the orbital revolution velocity and the coarse-dense stent can be produced by the provision of superelasticity to the hoselike body.

BRIEF DESCRIPTION OF THE DRAWINGS

FIG. 28 is a perspective view for illustrating the placement of the coarse-dense stent on the stent holding part in the embodiment according to the invention;

FIG. 29 is a diagram for illustrating a manner of placement of an elongated stent on the stent holding part in the embodiment according to the invention;

Figure 1A:
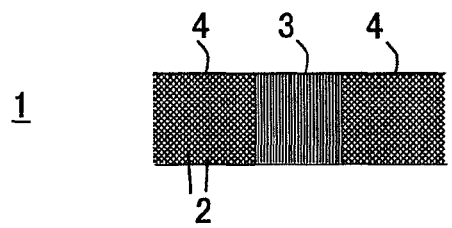
FIG. 1A is an enlarged side view of a stent of an embodiment according to the invention.

REFERENCE NUMERALS 1, 20, 30, 40, 48, 50, 60, 200 . . . stent, 2, 8, 212, 213 . . . thin wire, 3, 24, 34, 44, 54, 62 . . . thin wire densely braided hose portion, 4, 22, 26, 32, 36, 42, 46, 52, 56, 64 . . . thin wire coarsely braided hose portion, 10, 12, 14, 16 . . . hoselike body, 11, 13, 15, 17 . . . reticulated gap, 21 . . . elongate stent, 38 . . . coil, 58, 59 . . . thin wire densely braided end portion, 100, 112, 114 . . . blood vessel, 102, 108, 116 . . . blood vessel dilation, 104, 110 . . . main blood vessel, 106 . . . collateral vessel, 200 . . . continuous hoselike body braiding apparatus, 202 . . . main enclosure, 204 . . . meandering paths, 206 . . . carrier, 208, 209 . . . bobbin, 210 . . . twine guide bar, 214, 215 . . . carrier drive member, 216 . . . switching drive unit, 218 . . . switching arm, 219 . . . carrier holding part, 220 . . . winding shaft moving mechanism, 222 . . . winding shaft, 300 . . . microcatheter, 302 . . . guide wire, 310 . . . inner catheter part, 312 . . . inner catheter main body, 314, 316, 334 . . . marker, 318 . . . arrowhead part, 330 . . . outer sheath part, 332 . . . outer sheath main body, 336 . . . root part, 338 . . . molding jig bar, 340 . . . outer sheath extremity part, 350 . . . two-stage taper insertion jig, 352, 354 . . . tapered tube.

EMBODIMENTS FOR CARRYING OUT THE INVENTION

Hereinbelow, embodiments of the invention will be described in detail with reference to the drawings. Materials, shapes, sizes and the like that will be described below are mentioned by way of example, and details thereof can be appropriately modified according to a purpose of use.

Hereinbelow, similar elements will be designated by the same reference character and duplicative description thereof will be omitted. In the description, reference characters that will be formerly stated will be used later as required.

A term "superelastic metal" in the invention refers to various types of metal, such as nickel-titanium alloy, alloy with addition of copper, cobalt, chromium, iron and/or the like as necessary, and nickel-aluminium alloy, which are provided by heat treatment with superelastic property that offers an elasticity range five to ten times as wide as that of common metal, and that results in restoration to an original shape against great deformation.

Though various braiding methods for plaited cord may be used as a method of braiding "the hoselike body braided like knitting," the method has only to be that causing the individual thin wires to extend and finely gather when the resultant hoselike body is pulled in the longitudinal direction and causing resilient restoration to the original hoselike body when the body is released from pulling.

A thickness of the thin wires of metal, an outside diameter of the stent, an axial length of a thin wire densely braided hose portion and the like are appropriately designed according to an inside diameter of a blood vessel, a width of an opening of blood vessel dilation, positions of collateral vessels and the like.

In the description below, reference characters that have formerly been stated will be used later as required.

Embodiment 1

In a stent 1 of FIG. 1A, alternate twelve out of superelastic thin wires 2 (with a diameter of 0.03 mm) of nickel-titanium alloy are wound in the shape of a left-handed helix around a circumferential surface of a cylinder, the remaining twelve are wound in the shape of a right-handed helix, the left-handed thin wires 2 and the right-handed thin wires 2 are obliquely intersected like a plain weave and braided into a hoselike body having a specified length, an intermediate portion of the hoselike body is formed into a thin wire densely braided superelastic hose portion 3 in which mutually neighboring thin wires are in contact with each other or close to each other with a minute interspace, and both side portions thereof are formed into thin wire coarsely braided superelastic hose portions 4 in which mutually neighboring thin wires are provided with an interstice allowing passage of blood flow.

Referring to actual manufacturing processes, twenty-four thin wires 2 of titanium-titanium alloy without superelastic processing are placed in the shape of arcs in a knitting machine, alternate twelve out of the wires, and the remaining twelve, are guided onto a circumferential surface of a cylindrical metal mold in the shape of a left-handed helix and in the shape of a right-handed helix, respectively, braided into a coarsely braided hose with oblique intersections, and conveyed upward along the cylindrical metal mold. Deceleration in velocity of the conveyance for a short period in the middle of the conveyance causes the adjoining thin wires to contact with or approach each other so that the thin wires are braided into the densely braided hose portion, and the process of decelerating the conveyance velocity is intermittently repeated.

Once a continuous hoselike body is braided by repetition of such braiding by which the densely braided hose portion is placed between the coarsely braided hose portions, the continuous hoselike body is removed along with the cylindrical metal mold from the knitting machine, brought into a heat treatment chamber, and subjected to shape memory treatment therein by heating at 500° C. for 30 minutes, for instance. A transformation point is set at −10° C., for instance.

The continuous hoselike body that is provided with superelasticity by the heading processing is removed from the cylindrical metal mold and cut into the stents 1 of FIG. 1A.

In the stent 1, which is braided in such a knitting method as described above, the superelastic thin wires 2 wound helically are extended straight in general, and are formed into a bunch of the thin wires 2 (FIG. 1B) when pulled in the longitudinal direction and perform resilient restoration to the original state of FIG. 1A when released from pulling.

Figure 1B:
FIG. 1B is an enlarged side view of the same stretched in a longitudinal direction.
Figure 2A:
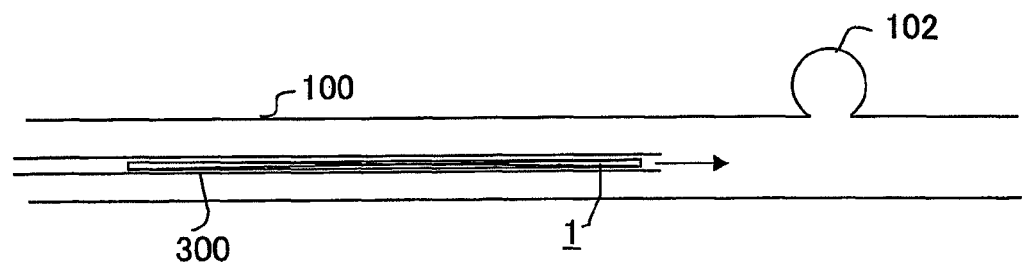
FIG. 2A is a schematic section of the stent of the embodiment according to the invention, the stent being guided into a blood vessel.

An example of the stent 1 of the above example used for closure of blood vessel dilation will be described with reference to FIGS. 2A and 2B. The stent 1 is gathered finely and extensively as shown in FIG. 1B by being pulled in the longitudinal direction and, in that state, is inserted into a microcatheter 300. The microcatheter 300 is inserted into a blood vessel 100 under guidance of a guide wire.

Figure 2B:
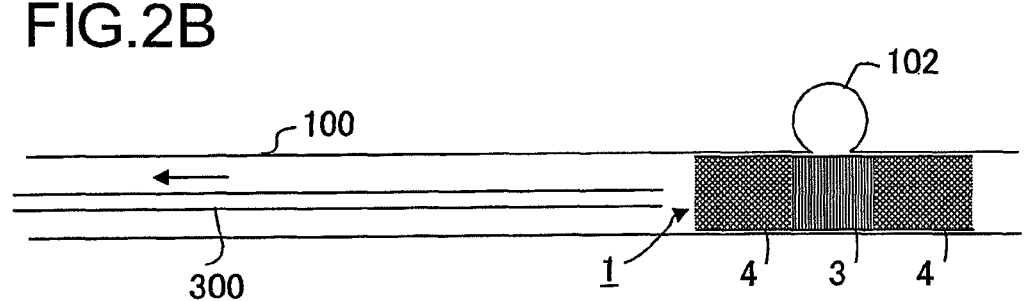
FIG. 2B is a schematic section of the stent set on an opening of blood vessel dilation.

Once an extremity of the microcatheter 300 advances to the vicinity of a blood vessel dilation 102, the stent 1 is pushed out of the extremity of the microcatheter 300 to an opening of the blood vessel dilation 102, so that the stent 1 performs resilient restoration to the original hoselike body and so that the opening of the blood vessel dilation 102 is closed by the thin wire densely braided hose portion 3 as shown in FIG. 2B. Thus blood is blocked from flowing into the blood vessel dilation 102, which is thereby prevented from rupturing of the blood vessel dilation 102.

Embodiment 2

Figure 3:
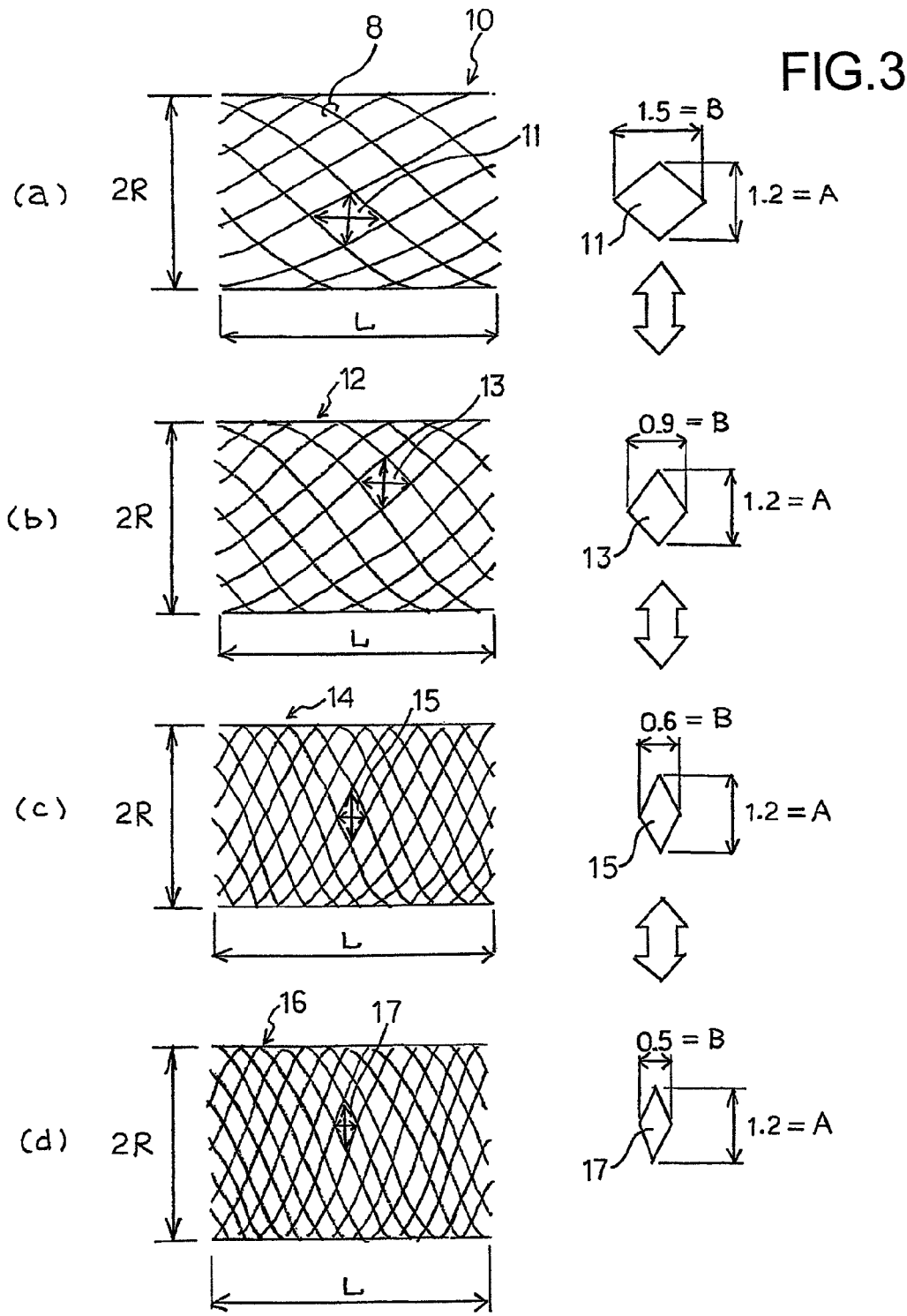
FIG. 3 are diagrams showing change in diamond-like reticulated gaps in the stent of the embodiment according to the invention.

Thin wires composed of shape memory material are fed into and braided by the knitting machine as described above, and then a hoselike body having reticulated gaps in the shape of diamond is formed as shown in FIG. 3. FIG. 3 show change in the diamond-shaped reticulated gaps in the hoselike body with respect to change in velocity of the conveyance in the knitting machine in a direction of braiding, that is, braiding velocity in the longitudinal direction of the hoselike body. The braiding velocity changes from high to low along a direction from FIG. 3(*a*) at top to FIG. 3(*d*) at bottom.

Referring to FIG. 3(*a*) at the top of FIG. 3, a radius of the hoselike body 10 is designated by reference character R and a length thereof in the longitudinal direction is designated by character L. In this example, the thin wires 8 described with reference to FIGS. 1, 2 are replaced by those having a diameter of 50 μm, and twelve thin wires 8 are loaded in the knitting machine for each of the left-handed helix and the right-handed helix. A length A of the diamond-like reticulated gap 11, formed between neighboring thin wires 8, along a circumferential direction of the hoselike body, is expressed by $(2R\pi)/12$ in calculation. In the above example, a relation $2R=5$ mm holds and results in the length A around 1.2 mm. The value of A undergoes no change according to the braiding velocity.

On the other hand, a length B of the diamond-like reticulated gap 11 along the longitudinal direction of the hoselike body is determined by the braiding velocity, i.e., becomes larger with increase in the braiding velocity. In the example of FIG. 3, the value B of a reticulated gap 11 in the hoselike body 10 of FIG. 3(*a*) is 1.5 mm, the value B of a reticulated gap 13 in a hoselike body 12 of FIG. 3(*b*) is 0.9 mm, the value B of a reticulated gap 15 in a hoselike body 14 of FIG. 3(*c*) is 0.6 mm, and the value B of a reticulated gap 17 in a hoselike body 16 of FIG. 3(*d*) is 0.5 mm.

Thus the length A of the diamond-like reticulated gap along the circumferential direction can be changed by change in number of the thin wires and diameter of the hoselike body, and the length B of the diamond-like reticulated gap along the longitudinal direction can be changed by change in the braiding velocity. An area of the opening of the diamond-like reticulated gap can be changed by those changes.

The following was found as a result of an examination on how fluid flowed out in the radial direction through the reticulated gaps on condition that the area of the opening of the diamond-like reticulated gap was changed. In the experiment, a vinyl tube having an inside diameter of about 5 mm was used as a main tube, an outer circumferential wall thereof was provided with an opening, and a branch tube was connected to the opening. The stent was placed so as to cover the opening, fluid was made to flow into one side of the main tube by an appropriate pump, and a rate of flow coming out of the other side of the main tube was compared with a rate of flow coming out of the branch tube. There were prepared several types of the stents of which the lengths B of the diamond-like reticulated gaps along the longitudinal direction were made to differ. The smallest of the values B was about 0.1 mm and there was additionally prepared the stent that had the neighboring thin wires in contact with each other, i.e., that substantially had the value B of zero. Three types of fluid having different viscosities, i.e., water, milk, and oil, were used.

In the result, outflow of the fluid to the branch tube was observed to one degree or another for any fluid even though the reticulated gaps of 0.1 mm were provided. For an open branch tube, namely, the outflow of the fluid is observed to some extent even though the stent is provided. In terms of a model of blood vessel, it can be considered that the stent does not completely block flow to collateral vessels.

Subsequently, an outlet of the open branch tube was closed so as to form modeled blood vessel dilation, and inflow and reflux of the fluid into and from the branch tube were examined. For the examination, both the main tube and the closed branch tube were filled with fluid without coloring before the placement of the stent, then the stent was placed so as to close the opening that communicates with the closed branch tube, and colored fluid was thereafter made to flow from one side of the main tube toward the other side thereof. With use of the stent having the value B of the reticulated gaps of 0.1 mm and the stent substantially having the value B of zero, the colored fluid hardly flowed into the closed branch tube and the inside of the closed branch tube was not colored. With use of other stents having the values B larger than 0.1 mm, the inside of the closed branch tube was colored simultaneously, in general, with the flow of the colored water through the stent in the longitudinal direction, so that occurrence of the inflow and reflux of the fluid into and from the closed branch tube through the reticulated gaps of the stent was found.

The results indicate that the inflow and reflux of the fluid into and from the closed branch tube can sufficiently be prevented with use of the stent having the length B of the reticulated gaps not larger than 0.1 mm along the longitudinal direction of the stent. The inside diameter of the tube of about 5 mm is in a range appropriate as an inside diameter of a blood vessel, the diameter of the thin wires of the stent of about 50 μm is in a range appropriate as that of proven material, and sizes of erythrocyte and leukocyte are known to be around 10 μm. It is therefore expected that inflow of blood into blood vessel dilation in a real blood vessel can effectively be blocked, while manufacture of the stent is facilitated by avoidance of excessive density of the gaps of the stent with the setting of the narrower size thereof being 0.1 mm or smaller.

On basis of findings obtained from these results of the experiment, it is understood that various aspects of blood vessel dilation can be treated by design in arrangement of coarseness and fineness of the reticulated gaps along the longitudinal direction of the stent. FIGS. 4 through 12 show several examples of the arrangement of coarseness and fineness of the reticulated gaps along the longitudinal direction of the stent.

Embodiment 3

Figure 4:
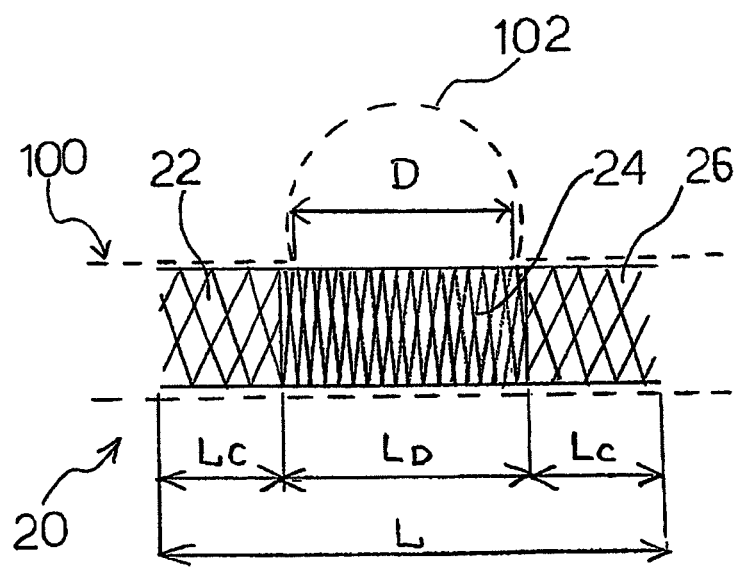
FIG. 4 is a diagram showing a configuration of the stent of the embodiment according to the invention.

FIG. 4 is a diagram showing a configuration of a stent 20 suitable for blood vessel dilation 102 in a blood vessel 100 with an opening having a size D. In the stent 20, a thin wire coarsely braided hose portion 22 having coarse reticulated gaps, a thin wire densely braided hose portion 24 having dense reticulated gaps, and a thin wire coarsely braided hose portion 26 having coarse reticulated gaps are formed in the stated order along the longitudinal direction of the stent 20. An overall length L of the stent 20 in the longitudinal direction is preferably about two times the size D of the opening of the blood vessel dilation 102 provided that the size D is known, for example.

As described above, the size B of the reticulated gaps of the thin wire densely braided hose portion 24 along the longitudinal direction of the stent 20 is preferably 0.1 mm or smaller. A length LD of the thin wire densely braided hose portion 24 along the longitudinal direction of the stent 20 is preferably not smaller than the size D of the opening of the blood vessel dilation 102. In the above example, the length LD can be about one-half of the overall length L of the stent 20.

The thin wire coarsely braided hose portions 22 and 26 preferably have the same length LC along the longitudinal direction of the stent 20. This makes it possible to place the thin wire densely braided hose portion 24 at a center along the longitudinal direction of the stent 20. The size B of the reticulated gaps in the thin wire coarsely braided hose portions 22 and 26 along the longitudinal direction of the stent 20 is preferably larger than 0.1 mm. Thus the stent 20 can be prevented from blocking blood flow to collateral vessels even if the collateral vessels exist in vicinity of the blood vessel dilation 102.

Figure 5:
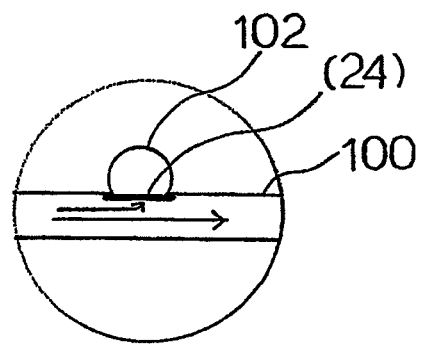
FIG. 5 is a diagram for illustrating a function of the stent of FIG. 4 that is used for treatment or the like of blood vessel dilation.

FIG. 5 is a schematic drawing for illustrating a function of the stent 20 used for treatment or the like of blood vessel dilation. The thin wire densely braided hose portion 24 of the stent 20 is placed in the blood vessel 100 so as to close the opening of the blood vessel dilation 102, so that blood flowing through the blood vessel 100 is blocked from entering into and circulating in the blood vessel dilation 102. Thus an excessive blood flow pressure can be prevented from being exerted on the blood vessel dilation 102. On condition that collateral vessels exist in vicinity of the blood vessel dilation 102, the provision of the thin wire coarsely braided hose portions 22 and 26 on both sides of the thin wire densely braided hose portion 24 keeps blood flow to the collateral vessels from being blocked.

Embodiment 4

Figure 6:
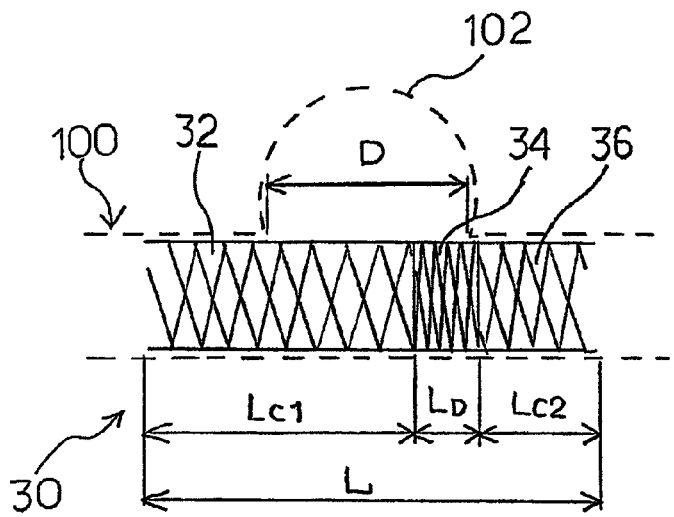
FIG. 6 is a diagram showing another configuration of a stent of the embodiment according to the invention.

FIG. 6 is a diagram showing a configuration of another stent 30 suitable for the blood vessel dilation 102 on the blood vessel 100 with the opening having the size D. A thin wire densely braided hose portion therein does not cover the whole opening of the blood vessel dilation 102 but covers part of the opening of the blood vessel dilation 102.

For the blood vessel dilation 102 that is formed on an outer circumference of the blood vessel 100 and that has the opening with the size D, observation on inflow of blood from the blood vessel 100 into the blood vessel dilation 102 shows that a large portion of the blood flow enters into the blood vessel dilation 102, circulates therein, and returns again into the blood vessel 100. That is, the returning portion exists in addition to a portion staying in the blood vessel dilation 102 and causes a blood flow pressure in the blood vessel dilation 102. The flow that enters into the blood vessel dilation 102 and returns again into the blood vessel 100 does not pass the whole plane in the opening of the blood vessel dilation 102 but enters into the blood vessel dilation 102 through a downstream side of the opening, circulates therein, and returns again into the blood vessel 100 through the upstream side of the opening, for instance. In some cases, as a matter of course, the flow may enter through the upstream side of the opening and may come out through the downstream side of the opening or may enter through a generally central part of the opening and may come out through a peripheral part of the opening.

In consideration of such facts, excessive increase in the blood flow pressure on the blood vessel dilation 102 can effectively be suppressed by placement of the thin wire densely braided hose portion such that part of the opening of the blood vessel dilation 102 is covered with the portion. In addition, such placement reduces the necessity to make the length of the thin wire densely braided hose portion of the stent accurately conform with the size of the opening of the blood vessel dilation 102, and facilitates manufacture of the stent 30.

In the stent 30 of FIG. 6, a thin wire coarsely braided hose portion 32 having coarse reticulated gaps, the thin wire densely braided hose portion 34 having dense reticulated gaps, and a thin wire coarsely braided hose portion 36 having coarse reticulated gaps, are formed in the stated order along the longitudinal direction of the stent 30. The overall length L of the stent 30 in the longitudinal direction is preferably about two times the size D of the opening of the blood vessel dilation 102 provided that the size D is known, for example. A position of the thin wire densely braided hose portion 34 along the longitudinal direction of the stent 30 is set with a deviation from a center position of the stent 30 toward the upstream side or downstream side. That is, lengths LC1 and LC2 of the thin wire coarsely braided hose portions 32 and 36 along the longitudinal direction are set at different values. In the example of FIG. 6, the length LC1 of the thin wire coarsely braided hose portion 32 on the upstream side along the longitudinal direction is larger than the length LC2 of the thin wire coarsely braided hose portion 36 on the downstream side along the longitudinal direction.

The length LD of the thin wire densely braided hose portion 34 along the longitudinal direction of the stent 30 is preferably set in a range from one-quarter to one-tenth of the overall length L of the stent 30 in the longitudinal direction. Considering that the stent 30 with the overall length L being about two times the length D of the opening of the blood vessel dilation 102 is placed in the blood vessel as described above, the length LD of the thin wire densely braided hose portion 34 corresponds to a range from D/2 to D/5. Even if the overall length L of the stent 30 deviates from the value 2D to some extent, the length LD of the thin wire densely braided hose portion 34 remains to be a portion of the length D of the opening of the blood vessel dilation 102. The length B of the reticulated gaps in the thin wire densely braided hose portion 34 along the longitudinal direction of the stent 30 is preferably not larger than 0.1 mm.

The length B of the reticulated gaps in the thin wire coarsely braided hose portions 32 and 36 along the longitudinal direction of the stent 30 is preferably larger than 0.1 mm and, more preferably herein, larger than a diameter of the catheter used for the treatment of the blood vessel dilation 102. The smallest diameter of the microcatheter used for the treatment of the blood vessel dilation 102 is currently in the order of 0.6 mm and, accordingly, the length B of the reticulated gaps in the thin wire coarsely braided hose portions 32 and 36 is preferably set to be not smaller than 0.6 mm. Though the length B of the reticulated gaps of the thin wire coarsely braided hose portions 32 and 36 on the upstream side is preferably set to be not smaller than 0.6 mm in the example of FIG. 6, the lengths B of the reticulated gaps in both the thin wire coarsely braided hose portions 32 and 36 are preferably set to be not smaller than 0.6 mm in consideration of the placement of the thin wire densely braided hose portion 34 on the upstream side of the opening, or in consideration of the placement of the thin wire densely braided hose portion 34 on the central part of the opening as described above.

Figure 7:
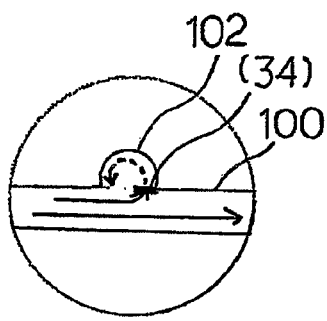
FIG. 7 is a diagram for illustrating a function of the stent of FIG. 6 that is used for treatment or the like of blood vessel dilation.
Figure 8:
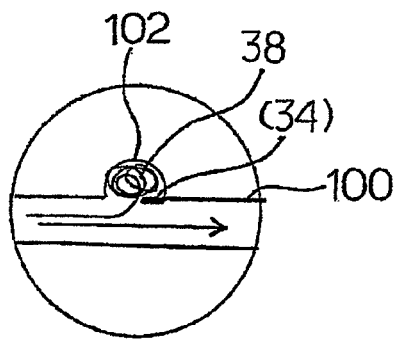
FIG. 8 is a diagram for illustrating another function of the stent of FIG. 6.

FIGS. 7 and 8 are schematic diagrams for illustrating functions of the stent 30 used for treatment or the like of blood vessel dilation. FIG. 7 shows one of the functions of the stent 30 in which the thin wire densely braided hose portion 34 is placed in the blood vessel 100 so as to partially close the opening of the blood vessel dilation 102 so that blood flow entering from the blood vessel 100 into the blood vessel dilation 102 and circulating therein can be effectively blocked. The function prevents an excessive blood flow pressure from being exerted on the blood vessel dilation 102.

FIG. 8 shows another one of the functions of the stent 30 in which a catheter for treatment is pierced from inside of the thin wire coarsely braided hose portion 32 of the stent 30 through a reticulated gap to outside of the stent. There is shown a process in which a coil 38 for insertion is detachably attached to the catheter for treatment, in which the catheter with the coil is fed from inside of the stent 30 through the reticulated gap to outside, i.e., into the blood vessel dilation 102 in FIG. 8, and in which the coil 38 is detached and implanted there. Such use of the stent 30 makes it possible to insert the catheter for treatment from inside of the stent 30 into the blood vessel dilation 102, for instance. With use of the catheter, the coil 38 for insertion can be made to pierce from inside of the stent 30 through the reticulated gap to outside of the stent 30. Thus an excessive blood flow pressure can be prevented from being exerted on the blood vessel dilation 102 with use of the coil implanting method, if necessary.

Embodiment 5

Figure 9:
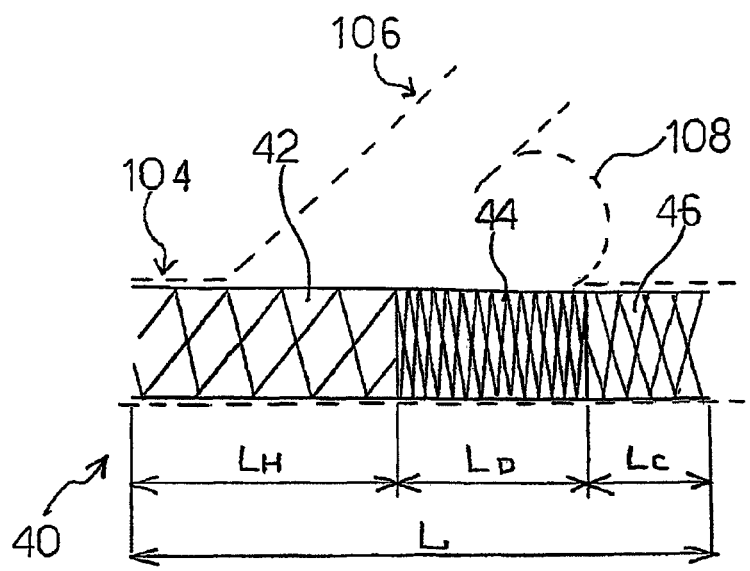
FIG. 9 is a diagram showing still another configuration of a stent of the embodiment according to the invention.

FIG. 9 is a diagram showing a configuration of a stent 40 suitable for blood vessel dilation stretching from a main blood vessel to a collateral vessel. In the example shown herein, a collateral vessel 106 branches from a main blood vessel 104, and blood vessel dilation 108 is formed therebetween. In the stent 40, a first thin wire coarsely braided hose portion 42 having coarse reticulated gaps, a thin wire densely braided hose portion 44 having dense reticulated gaps, and a second thin wire coarsely braided hose portion 46 having coarse reticulated gaps are formed in the stated order along a longitudinal direction of the stent 40.

The reticulated gaps of the first thin wire coarsely braided hose portion 42 are made more coarse than the reticulated gaps of the second thin wire coarsely braided hose portion 46. That is, the length B of the reticulated gaps in the second thin wire coarsely braided hose portions 46 along the longitudinal direction of the stent 40 is set to such an extent that blocking of blood flow is avoided, i.e., in the order of a little more than 0.1 mm, and the length B of the reticulated gaps in the first thin wire coarsely braided hose portions 42 along the longitudinal direction of the stent 40 is set to such an extent that another stent can be pierced therethrough.

On condition that the length B of the reticulated gaps through which the catheter for the coil 38 is to be pierced is 0.6 mm as described above, for example, the length B of the reticulated gaps in the second thin wire coarsely braided hose portion 46 along the longitudinal direction of the stent 40 is preferably set to be larger than 0.1 mm and not larger than 0.6 mm. The length B of the reticulated gaps in the first thin wire coarsely braided hose portion 42 along the longitudinal direction of the stent 40 is set to be larger than 0.6 mm and generally as large as an inside diameter of the collateral vessel 106. On condition that the inside diameter of the collateral vessel 106 is 1 mm, for example, the length B of the reticulated gaps in the first thin wire coarsely braided hose portion 46 along the longitudinal direction of the stent 40 is set in the order of 1 mm.

The length LD of the thin wire densely braided hose portion 44 along the longitudinal direction of the stent 40 is preferably set at a length that generally covers an opening of the blood vessel dilation 108 extending from a branch point of the collateral vessel 106. A length LH of the first thin wire coarsely braided hose portion 42 along the longitudinal direction of the stent 40 is preferably set so as to sufficiently cover an opening of the main blood vessel 104 from which the collateral vessel 106 branches.

Figure 10:
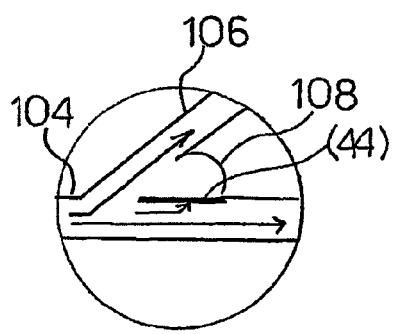
FIG. 10 is a diagram for illustrating a function of the stent of FIG. 9 that is used for treatment or the like of blood vessel dilation.
Figure 11:
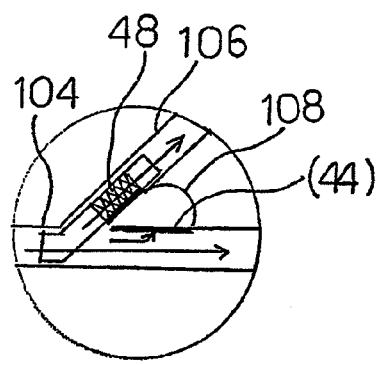
FIG. 11 is a diagram for illustrating another function of the stent of FIG. 9.

FIGS. 10 and 11 are schematic diagrams for illustrating functions of the stent 40 used for treatment or the like of blood vessel dilation. FIG. 10 shows one of the functions of the stent 40 in which the thin wire densely braided hose portion 44 is placed in the blood vessel 104 so as to close the opening of the blood vessel dilation 108 in the main blood vessel 104 so that blood flow entering from the blood vessel 104 into the blood vessel dilation 108 and circulating therein can be effectively blocked. The function prevents an excessive blood flow pressure from being exerted on the blood vessel dilation 108. FIG. 11 shows another one of the functions of the stent 40 in which another stent 48 is inserted through a reticulated gap of the thin wire coarsely braided hose portion 42 of the stent 40 into the collateral vessel 106 so as to be implanted therein. This another stent 48 closes the opening of the blood vessel dilation 108 in the collateral vessel 106 so that blood flow entering from the collateral vessel 106 into the blood vessel dilation 108 and circulating therein can be effectively blocked.

Embodiment 6

Figure 12:
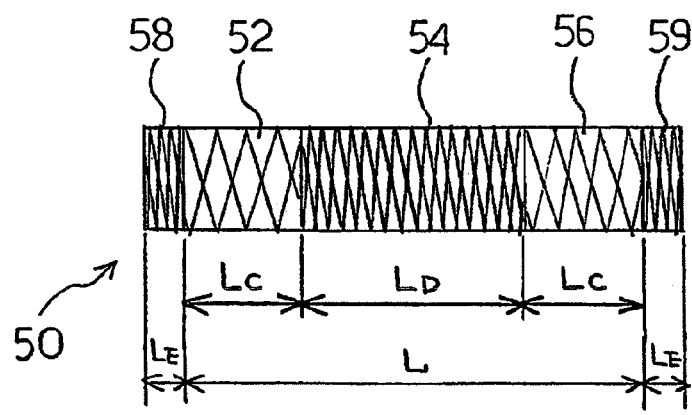
FIG. 12 is a diagram showing another configuration of a stent of the embodiment according to the invention.

When a stent is implanted in a blood vessel with use of a microcatheter or the like as described above, the stent is detachably held on an extremity of a guide wire or the like. FIG. 12 is a diagram showing a structure of a stent by which reliability of attachment and detachment of the stent can be improved when the stent is detachably held on a guide wire or the like.

The stent 50 corresponds to the stent 20 which has been described with reference to FIG. 4 and in which thin wire densely braided end portions with a manner of braiding denser than that for the thin wire coarsely braided hose portions are provided at both ends of the stent. In the stent 50, namely, a thin wire coarsely braided hose portion 52 having coarse reticulated gaps, a thin wire densely braided hose portion 54 having dense reticulated gaps, and a thin wire coarsely braided hose portion 56 having coarse reticulated gaps are formed in the stated order along a longitudinal direction of the stent 50, a thin wire densely braided end portion 58 is additionally provided outside the thin wire coarsely braided hose portion 52, and a thin wire densely braided end portion 59 is additionally provided outside the thin wire coarsely braided hose portion 56.

A manner of braiding the thin wire densely braided end portions 58 and 59 provided at both the ends of the stent 50 is made denser than that for the thin wire densely braided hose portion 54 so as to resist raveling of the thin wires. That is, the length B of the reticulated gaps in the thin wire densely braided end portions 58, 59 along the longitudinal direction of the stent 50 is set smaller than the length B of the reticulated gaps in the thin wire densely braided hose portion 54. For the purpose of resisting raveling of the thin wires, the length B of the reticulated gaps may be substantially zero, for instance. This facilitates holding of the stent on the extremity of the guide wire. A length LE of the thin wire densely braided end portions 58, 59 along the longitudinal direction of the stent 50 can be set according to a length of an attachment part of the guide wire.

Embodiment 7

Figure 13:
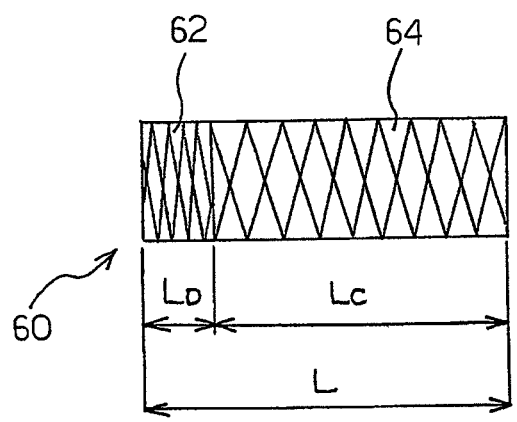
FIG. 13 is a diagram showing still another configuration of a stent of the embodiment according to the invention.
Figure 14:
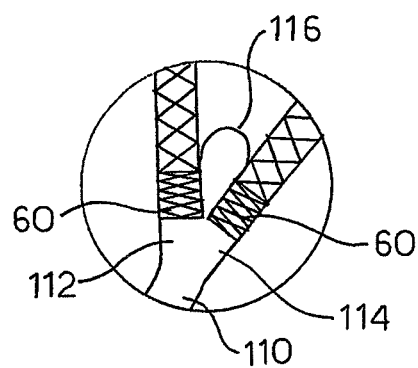
FIG. 14 is a diagram for illustrating a function of the stent of FIG. 13.

FIGS. 13 and 14 are diagrams showing a configuration of a stent 60 suitable for blood vessel dilation existing at a fork in a blood vessel. In the example shown herein, a main blood vessel 110 is forked into two branch vessels 112 and 114, and blood vessel dilation 116 is formed at the fork. In the stent 60, a first thin wire densely braided hose portion 62 having dense reticulated gaps and a thin wire coarsely braided hose portion 64 having coarse reticulated gaps are formed in the stated order along a longitudinal direction of the stent 60. With use of a pair of the stents 60, the thin wire densely braided hose portions 62 of both the stents are placed so as to be applied on an opening at the fork having the blood vessel dilation 116.

As described with reference to FIG. 4, the size B of reticulated gaps of the thin wire densely braided hose portion 62 along the longitudinal direction of the stent 60 is preferably 0.1 mm or smaller. The length LD of the thin wire densely braided hose portion 62 along the longitudinal direction of the stent 60 is preferably not smaller than a length of the common opening of the blood vessels 112 and 114 at the fork of the main blood vessel 110. In the above example, the length LD can be about a quarter of the overall length L of the stent 60.

As described with reference to FIG. 4, the size B of the reticulated gaps of the thin wire coarsely braided hose portion 64 along the longitudinal direction of the stent 60 is preferably larger than 0.1 mm. Thus the stent 60 can be prevented from blocking blood flow to collateral vessels even if the collateral vessels exist in the vicinity of the blood vessel dilation 116 on the blood vessels 112 and 114.

Embodiment 8

Production of a coarse-dense stent having the thin wire coarsely braided hose portions and the thin wire densely braided hose portions requires the use of thin wires made of shape memory material, to braid on a shaping jig at normal temperature a continuous hoselike body having arrangement of coarse reticulations and dense reticulations along an axial direction, and to provide superelasticity by heat treatment of the braided continuous hoselike body along with the shaping jig.

Figure 15:
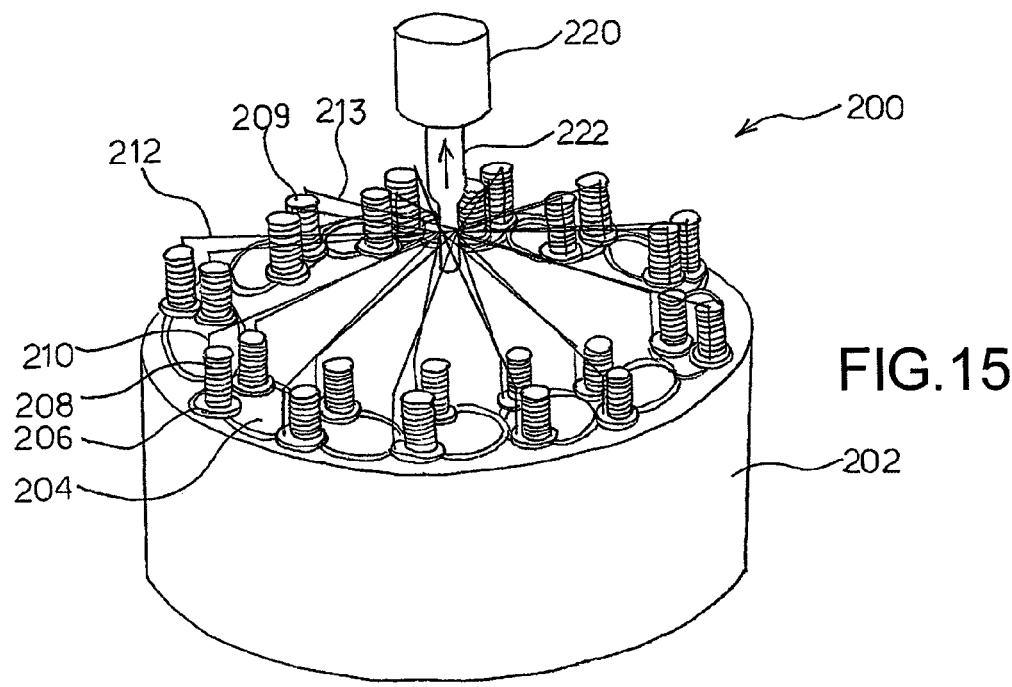
FIG. 15 is a diagram for illustrating a configuration of a continuous hoselike body braiding apparatus of the embodiment according to the invention.

FIG. 15 is a diagram illustrating a configuration of a continuous hoselike body braiding apparatus 200 that is capable of braiding a continuous hoselike body, on a winding shaft, with arbitrary arrangement of coarseness and denseness in an axial direction thereof. In the continuous hoselike body braiding apparatus 200, a mechanism of a plaited-cord manufacturing apparatus that has conventionally been used for braiding a plaited-cord is utilized and improved for braiding the continuous hoselike body, and a control sequence thereof is configured afresh so that intervals of reticulations in the continuous hoselike body can be set with the arbitrary arrangement of coarseness and denseness along a longitudinal direction of the continuous hoselike body.

The continuous hoselike body braiding apparatus 200 contains various drive units and control units and includes a main enclosure 202 serving as a base of the whole apparatus, and a winding shaft moving mechanism 220 that is placed above the main enclosure 202 and that moves a winding shaft 222 in the axial direction thereof. In FIG. 15, an external shape of the main enclosure 202 is shown like a cylinder, and the winding shaft 222 is placed on a center axis of the cylinder-like enclosure. The winding shaft 222 corresponds to the shaping jig for the heat treatment for providing superelasticity.

In two meandering paths 204 provided on a top surface of the main enclosure 202, a plurality of figure-of-8-like meandering travel paths are provided so as to circle around generally and continuously, and thus the paths meander and circle around while crossing each other. In the example of FIG. 15 six meandering travel paths shaped like a FIG. 8 are provided, and they are continuously placed around the center axis of the main enclosure 202 so as to form the two meandering paths 204 as a whole.

Carriers 206 are each integrated with a bobbin 208, 209 and are intended to convey the bobbins along the meandering paths 204. A manner in which the carriers 206 and the bobbins 208, 209 are conveyed along the meandering paths 204 will be described later in detail.

The bobbin 208, 209 is a cylindrical thin wire bobbin on which a thin wire 212, 213 composed of shape memory material is wound in advance. A twine guide bar 210 is integrally fixed to each bobbin 208, 209. Each bobbin 208, 209 can be rotated about a center axis thereof.

The thin wire 212, 213 wound around each bobbin 208, 209 is unwound and guided by the twine guide bar 210, and an extremity of the unwound thin wire 212, 213 is initially wound around the winding shaft 222. When the bobbins 208, 209 subsequently travel around the winding shaft 222 along the meandering paths 204, i.e., make orbital motions about the winding shaft 222 as an axis of orbit, the thin wires 212, 213 are sequentially wound around the winding shaft 222, and the thin wires 212, 213 wound around the bobbins 208, 209 are unwound sequentially and simultaneously with rotation of the bobbins 208, 209 about the center axes thereof.

In the example of FIG. 15 twenty-four bobbins 208, 209 are provided, of which twelve bobbins 208 are right-handed revolution bobbins for making right-handed orbital motions about the winding shaft 222 while making meander motions along the meandering paths 204, and the remaining twelve bobbins 209 are left-handed revolution bobbins for making left-handed orbital motions about the winding shaft 222 while making meander motions along the meandering paths 204. Herein, the term "right-handed revolution" refers to clockwise revolution about the winding shaft 222 and the term "left-handed revolution" refers to counterclockwise revolution about the winding shaft 222 in viewing from upwardness. Likewise, the terms "right-handedly wound" and "left-handedly wound" refer to clockwise and counterclockwise winding, respectively, around the winding shaft 222 in viewing from upwardness.

The thin wires 212 drawn from the right-handed revolution bobbins 208 are right-handedly wound around the winding shaft 222 and the thin wires 213 drawn from the left-handed revolution bobbins 209 are left-handedly wound around the winding shaft 222. With lifting of the winding shaft 222 along the axis of orbit in a direction of an arrow shown in FIG. 15, each of the right-handedly wound thin wires 212 and corresponding each of the left-handedly wound thin wires 213 undergo mutual oblique crossing like plain weave, so that a hoselike body having an inside diameter as large as a diameter 2R of the winding shaft 222 is braided along the axial direction while the diamond-shaped reticulated gaps are formed.

Figure 16:
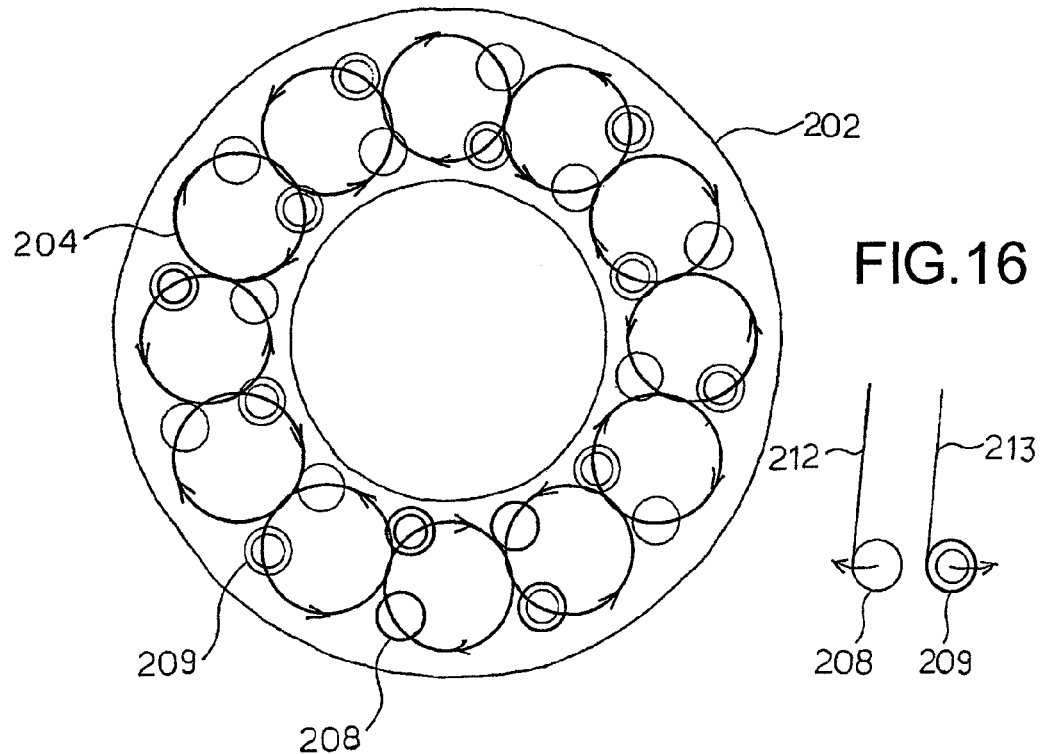
FIG. 16 is a diagram for schematically illustrating placement of meandering paths and bobbins in the continuous hoselike body braiding apparatus of the embodiment according to the invention.

FIG. 16 is a diagram schematically illustrating placement of the meandering paths 204 on the top surface of the main enclosure 202 and the bobbins 208, 209. As described above, the meandering paths 204 are formed by the continuous placement of six meandering travel paths shaped like a figure 8 around the axis of orbit. The meandering path shaped like a figure 8 is configured by continuation of two circular travel paths, and thus twelve circular travel paths are shown in the example of FIG. 16. In each of the circular travel paths, directions in which the bobbins 208, 209 travel are shown by arrows. In each of the twelve circular travel paths are provided one right-handed revolution bobbin 208 and one left-handed revolution bobbin 209.

On the right side of FIG. 16 are shown a relation between the traveling direction of the right-handed revolution bobbin 208 and a manner of unwinding of the thin wire 212, and a relation between the traveling direction of the left-handed revolution bobbin 209 and a manner of unwinding of the thin wire 213. In this manner, the right-handed revolution bobbin 208 and the left-handed revolution bobbin 209 differ in the manner of unwinding the thin wire 212, 213 according to the traveling directions thereof.

Figure 17:
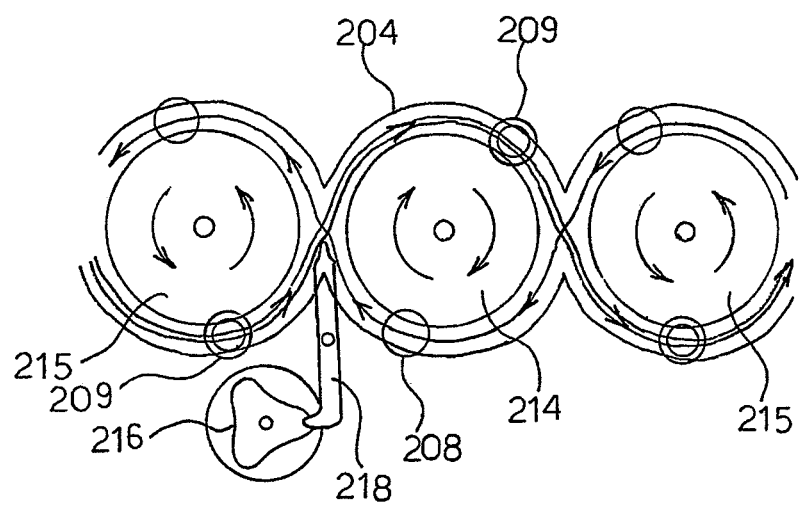
FIG. 17 is a diagram showing in detail a portion of the meandering paths in the continuous hoselike body braiding apparatus of the embodiment according to the invention.
Figure 18:
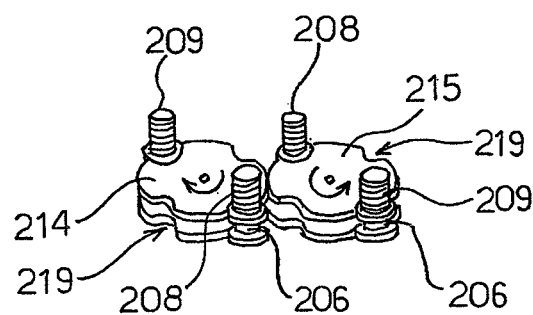
FIG. 18 is a perspective view showing in detail a portion of the meandering paths in the continuous hoselike body braiding apparatus of the embodiment according to the invention.

FIGS. 17 and 18 are detailed diagrams for illustrating a manner in which the carriers 206 and the bobbins 208, 209 loaded thereon are conveyed along the meandering paths 204. FIG. 17 is a diagram illustrating details of a portion of the meandering paths 204 on the top surface of the main enclosure 202 and FIG. 18 is a perspective view of the portion of the meandering paths 204.

The two meandering paths 204 are guide grooves provided on a top plate of the main enclosure 202. In the guide grooves, as described above, the twelve circular travel paths are continuously connected. As shown in FIG. 18, carrier drive members 214, 215 provided inside the circular travel paths are disc-like members on which carrier holding parts 219 are provided as depressions for holding and conveying the carriers 206. The carrier drive members 214, 215 are provided one by one for each circular travel path and are driven to rotate about the center axes thereof by driver units not shown.

In the rotational drive of the carrier drive members 214, 215, adjoining carrier drive members are rotated at the same velocity and in directions opposite to each other. In FIGS. 17 and 18, for instance, the carrier drive members 214 rotate right-handedly about the center axes thereof and then the carrier drive members 215 adjoining the members 214 rotate left-handedly about the center axes thereof.

As shown in FIG. 17, accordingly, the bobbins 208, 209 are conveyed with right-handed revolution on the circular travel paths by the carrier drive members 214 and with left-handed revolution on the circular travel paths by the carrier drive members 215. In FIG. 16, the traveling directions of the bobbins 208, 209 along the circular travel paths are shown by the arrows, and the traveling directions along adjoining circular travel paths are shown as revolution directions opposite to each other.

A switching drive unit 216 and a switching arm 218 shown in FIG. 17 are a switching mechanism having a function of switching the carriers 206 and the bobbins 208, 209, conveyed by the carrier drive members 214, 215, from one of the two meandering paths 204 to the other at a figure-of-8-like intersecting position where the two meandering paths 204 intersect. That is, the mechanism has the function of switching from the carrier holding part of one of the carrier drive members 214, 215 to the carrier holding part of the adjoining carrier drive member in a direction without change in the traveling direction of a carrier 206 held by the carrier holding part 219 and the bobbins 208, 209 loaded thereon which have just reached the figure-of-8-like intersecting position with rotation timing of the carrier drive members 214, 215.

In the example of FIG. 17, for instance, when the bobbin 208 conveyed right-handedly by the right-handedly rotating carrier drive member 214 at the center of three carrier drive members shown therein circles right-handedly on the drawing and reaches the figure-of-8-like intersecting position on the left side, the switching drive unit 216 is activated to move an extremity of the switching arm 218. The movement of the extremity of the switching arm 218 acts so that the bobbin 208 passes the figure-of-8-like intersecting position on the left side from the underside of the right-handedly rotating carrier drive member 214 at the center, and travels from the right side to the upper side of the left-handedly rotating carrier drive member 215 on the left side on the drawing. In the example of FIG. 17, when the bobbin 209 conveyed left-handedly by the left-handedly rotating carrier drive member 215 on the left side circles left-handedly on the drawing and reaches the figure-of-8-like intersecting position on the right side, the switching drive unit 216 is activated to move the extremity of the switching arm 218. The movement of the extremity of the switching arm 218 on this occasion acts so that the bobbin 209 passes the figure-of-8-like intersecting position on the right side from the underside of the left-handedly rotating carrier drive member 215 on the left side and travels from the left side to the upper side of the right-handedly rotating carrier drive member 214 on the right side on the drawing.

In this manner, the right-handed revolution bobbin 208 and the left-handed revolution bobbin 209 are transferred at the figure-of-8-like intersecting position between the adjoining carrier drive members 214, 215 by the switching mechanism so that courses thereof intersect. Though only the one switching mechanism corresponding to the one figure-of-8-like intersecting position is shown in FIG. 17, a similar switching mechanism is provided corresponding to each of the figure-of-8-like intersecting positions. In FIG. 18 the switching mechanism is omitted.

With the rotation of the carrier drive members 214, 215 at the same velocity in the directions opposite to each other and the activation of the switching mechanisms with satisfactory timing as described above, the right-handed revolution bobbins 208 make the right-handed orbital motions about the axis of orbit while making the meandering motions, and the left-handed revolution bobbins 209 make the left-handed orbital motions about the axis of orbit while making the meandering motions. When the extremities of the thin wires 212, 213 drawn from the bobbins 208, 209 are wound around the winding shaft 222 provided on the axis of orbit, the thin wires 212 drawn from the bobbins 208 are right-handedly wound around the winding shaft 222 and the thin wires 213 drawn from the bobbins 209 are left-handedly wound around the winding shaft 222.

The two meandering paths 204, the carrier drive members 214, 215, the switching drive unit 216 and the switching arm 218 that are the switching mechanism, the carriers 206, and the carrier holding parts 219 provided in the carrier drive members 214, 215, which have been described above, are elements constituting a thin wire drive mechanism for driving the thin wire bobbins that are the bobbins 208, 209. As described above, the thin wire drive mechanism causes the bobbins 208, which are the twelve right-handed revolution thin wire bobbins, to make the right-handed orbital motions about the axis of orbit at an orbital revolution velocity along one of the two meandering paths 204 provided around the axis of orbit and meandering with intersections, and causes the bobbins 209, which are the twelve left-handed revolution thin wire bobbins, to make the left-handed orbital motions about the axis of orbit at the orbital revolution velocity along the other of the two meandering paths 204.

The orbital revolution velocity of the bobbins 208, 209 is determined by the rotational velocity of the carrier drive members 214, 215 and a total number of the carrier drive members 214, 215 placed around the axis of orbit. The rotational velocity of the carrier drive members 214, 215 can be changed by control over the driver units not shown. A moving velocity of the winding shaft 222 in the axial direction, which constitutes a braiding velocity, can be changed by control over the winding shaft moving mechanism 220 as described above.

On the assumption that the orbital revolution velocity is constant, increase in the moving velocity of the winding shaft 222 in the axial direction thereof, i.e., increase in the braiding velocity causes increase in braiding pitch of the continuous hoselike body along the longitudinal direction, and increase in roughness of the braiding. On the assumption that the orbital revolution velocity is constant, decrease in the braiding velocity causes decrease in the braiding pitch of the continuous hoselike body along the longitudinal direction, and increase in denseness of the braiding, by contrast.

On the assumption that the braiding velocity is constant, decrease in the orbital revolution velocity causes increase in the braiding pitch of the continuous hoselike body along the longitudinal direction and increase in roughness of the braiding. On the assumption that the braiding velocity is constant, increase in the orbital revolution velocity causes decrease in the braiding pitch of the continuous hoselike body along the longitudinal direction and increase in denseness of the braiding, in contrast to that.

In the continuous hoselike body braiding apparatus 200 having the above configuration, a continuous hoselike body can be braided with arbitrary arrangement of coarseness and denseness in the axial direction thereof by control through the control unit over the operation of the thin wire bobbin drive mechanism including the carrier drive members 214, 215 and the winding shaft moving mechanism 220 for moving the winding shaft 222 in the axial direction. That is, increase in ratio of the moving velocity in the axial direction to the orbital revolution velocity results in formation of the thin wire coarsely braided hose portion having a large opening area of the reticulated gaps with coarse braiding, along the longitudinal direction of the hoselike body. On the other hand, decrease in the ratio of the moving velocity in the axial direction to the orbital revolution velocity results in formation of the thin wire densely braided hose portion having a smaller opening area of the reticulated gaps with denser braiding than the thin wire coarsely braided hose portion, along the longitudinal direction of the hoselike body. By an arrangement in a predetermined time series of high-velocity braiding periods in which the ratio of the moving velocity in the axial direction to the orbital revolution velocity is increased and low-velocity braiding periods in which the ratio of the moving velocity in the axial direction to the orbital revolution velocity is decreased, a coarse-dense continuous hoselike body including at least one thin wire coarsely braided hose portion and at least one thin wire densely braided hose portion arranged in an order of predetermined lengths of the thin wire coarsely braided hose portion and the thin wire densely braided hose portion can be braided around the winding shaft.

Embodiment 9

Figure 19:
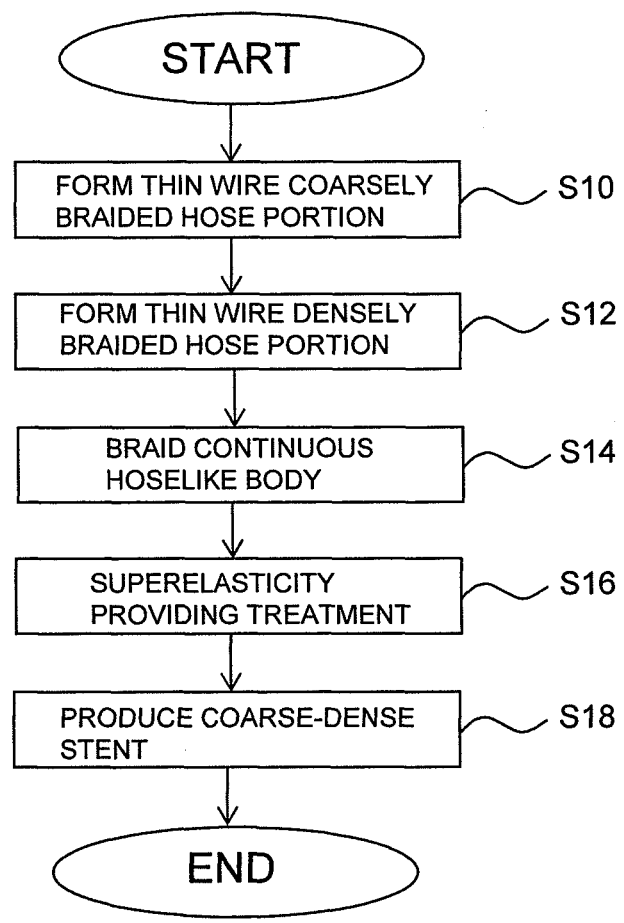
FIG. 19 is a flow chart for illustrating a procedure for producing the stent provided with superelasticity with use of the continuous hoselike body braiding apparatus in the embodiment according to the invention.

FIG. 19 is a flow chart illustrating a procedure for producing the coarse-dense stent provided with superelasticity with use of the continuous hoselike body braiding apparatus 200 described with reference to FIGS. 15-18. The term "coarse-dense stent" refers to a stent in which portions with coarse braiding and portions with dense braiding are placed along an axial direction of the stent.

In order to produce the coarse-dense stent, the continuous hoselike body braiding apparatus 200 is used, and the thin wire coarsely braided hose portion in which the reticulated gaps having large opening areas are formed with coarse braiding is formed along the longitudinal direction of the hoselike body, with the increase in the ratio of the moving velocity in the axial direction to the orbital revolution velocity (S10). The thin wire densely braided hose portion in which the reticulated gaps having smaller opening areas with denser braiding than the thin wire coarsely braided hose portion are formed is formed along the longitudinal direction of the hoselike body, with the decrease in the ratio of the moving velocity in the axial direction to the orbital revolution velocity (S12).

For example, FIGS. 3(a) through 3(d) described before show the change from coarse braiding to dense braiding that results from change from high to low braiding velocity, that is, the moving velocity in the axial direction on the assumption that the orbital revolution velocity is constant.

These two steps are combined by an arrangement in a predetermined time series of the high-velocity braiding periods in which the ratio of the moving velocity in the axial direction to the orbital revolution velocity is increased and the low-velocity braiding periods in which the ratio of the moving velocity in the axial direction to the orbital revolution velocity is decreased, and the coarse-dense continuous hoselike body including at least one thin wire coarsely braided hose portion and at least one thin wire densely braided hose portion arranged in an order of predetermined lengths of the thin wire coarsely braided hose portion and the thin wire densely braided hose portion is braided around the winding shaft (S14). Thus the coarse-dense continuous hoselike body having a predetermined arrangement of coarse braiding and dense braiding is braided on the winding shaft 222.

In FIG. 4 described before, for instance, the stent 20 is shown in which the thin wire coarsely braided hose portion 22 having the length LC, the thin wire densely braided hose portion 24 having the length LD, and the thin wire coarsely braided hose portion 26 having the length LC are continuously placed. In FIG. 12 there is shown the stent 50 in which the thin wire densely braided end portion 58 having the length LE with the densest braiding, the thin wire coarsely braided hose portion 52 having the length LC, the thin wire densely braided hose portion 54 having the length LD, the thin wire coarsely braided hose portion 56 having the length LC, and the thin wire densely braided end portion 59 having the length LE with the densest braiding are continuously placed.

Referring again to FIG. 19, the coarse-dense continuous hoselike body having been braided is removed from the continuous hoselike body braiding apparatus 200, while a state of the hoselike body wound around the winding shaft 222 is maintained, and is subjected to the superelasticity providing treatment by heating exceeding the transformation point of the thin wires composed of shape memory material (S16). After that, the temperature of the continuous hoselike body wound around the winding shaft 222 is returned to normal. Then the continuous hoselike body is removed from the winding shaft 222 and the coarse-dense stent provided with superelasticity is thereby produced (S18).

The superelasticity providing treatment is also called shape memory treatment, and is heat treatment in which processed shape memory material is restrained in shape by the shaping jig or the like and is held at 400 to 500° C. for several minutes to one hour, for instance. With the shape restraining heat treatment, the processed product removed from the shaping jig acquires a superelastic property such that the product, used in an austenite phase state with a temperature higher than a shape recovery temperature of the shape memory material and deformed, instantaneously recovers an original shape thereof upon removal of an external force having caused the deformation.

In the above example, the winding shaft 222 corresponds to the shaping jig, and the continuous hoselike body is provided with the superelastic property by the superelasticity providing treatment for the continuous hoselike body wound around the winding shaft 222. That is, the continuous hoselike body returned to the normal temperature, removed from the winding shaft 222, and deformed after the superelasticity providing treatment instantaneously recovers the same shape as that of the hoselike body wound around the winding shaft 222 upon removal of the external force having caused the deformation.

The heat treatment for providing superelasticity may be performed at 500° C. for 30 minutes with use of nickel-titanium alloy, as the shape memory material, that allows the shape recovery temperature to be not higher than a room temperature, for instance.

Thus the coarse-dense stent provided with superelasticity is, ordinarily, the coarse-dense continuous hoselike body having an inside diameter as large as a diameter of the winding shaft 222 at normal temperature, can be considerably decreased in outside diameter by being elongated in the axial direction, for example, and has a property of immediately returning to the original coarse-dense continuous hoselike body having the inside diameter as large as the diameter of the winding shaft 222 upon subsequent removal of the external force having caused the elongation. In an example, the length of 15 mm of the stent in a normal state can be elongated to about 50 mm and the outside diameter of 5 mm thereof can thereby be reduced to about 0.9 mm. Then the removal of the external force having caused the elongation in the axial direction immediately results in recovery of the original length of 15 mm and the original outside diameter of 5 mm.

Embodiment 10

Figure 20:
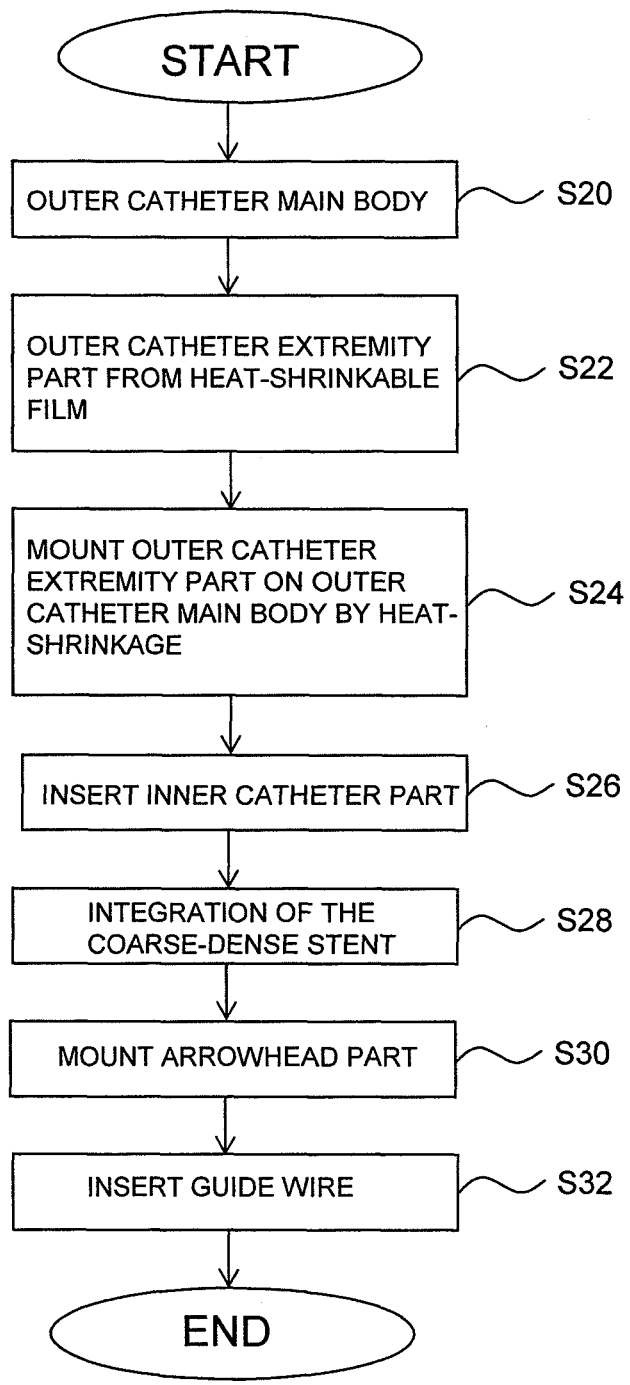
FIG. 20 is a flow chart showing a procedure for forming the microcatheter using the stent provided with superelasticity in the embodiment according to the invention.
Figure 30:
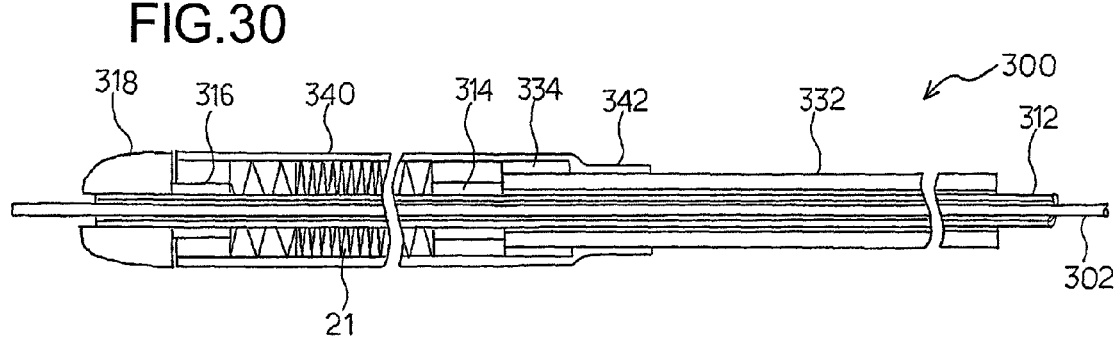
FIG. 30 is a diagram for illustrating a state in which the inner catheter part has been formed in the embodiment according to the invention.
Figure 31:
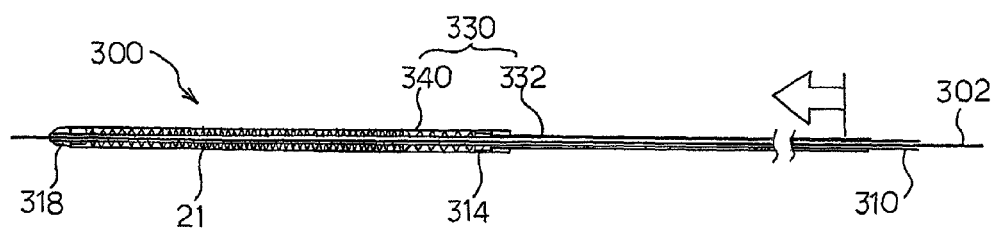
FIG. 31 is a diagram for illustrating the microcatheter in a return mode that uses the stent provided with superelasticity in the embodiment according to the invention.
Figure 32:
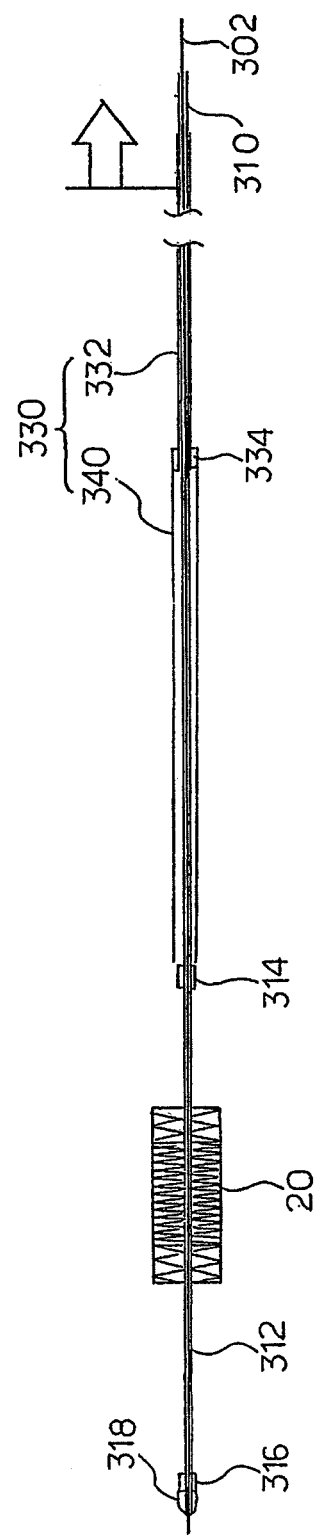
FIG. 32 is a diagram for illustrating the microcatheter in a push-in mode that uses the stent provided with superelasticity in the embodiment according to the invention.

A microcatheter can be formed with use of the coarse-dense stent provided with superelasticity. Hereinbelow will be described a manner of forming the microcatheter for holding the coarse-dense stent provided with superelasticity, with use of a flow chart shown in FIG. 20 and of FIGS. 21 through 32. FIG. 20 is the flow chart showing a procedure for forming the microcatheter using the coarse-dense stent provided with superelasticity. FIGS. 21 through 24 are diagrams sequentially illustrating a manner of forming an outer sheath part. FIGS. 25 through 30 are diagrams for sequentially illustrating a procedure for inserting an inner catheter part into the outer sheath part and making the inner catheter part hold the coarse-dense stent provided with superelasticity. FIGS. 31 and 32 are a general view of the microcatheter using the coarse-dense stent provided with superelasticity and a diagram for illustrating functions thereof, respectively. In these drawings, magnification of parts required for illustration makes scales thereof different from reality.

Figure 21:
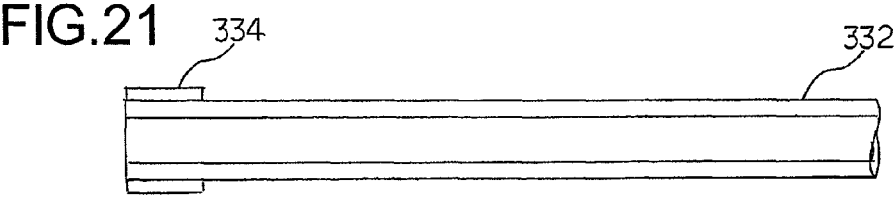
FIG. 21 is a diagram for illustrating an appearance of an outer sheath main body in the embodiment according to the invention.

As shown in FIG. 20, an outer sheath main body is initially prepared for formation of the microcatheter (S20). FIG. 21 is a diagram showing an appearance of the outer sheath main body 332 having a marker 334 mounted on an extremity thereof. The outer sheath main body 332 is a flexible tube having a slide passage in which an inner catheter main body 312 that will be described later is housed so as to be slidable in the axial direction. An inside diameter part of the tube corresponds to the slide passage.

As the outer sheath main body 332 it is possible to use a nylon tube which is selected for medical use and in which stainless reticulations are embedded. In an example of sizes thereof, an outside diameter is 0.8 mm, an inside diameter is 0.46 mm, a tube wall thickness of the tube is 170 μm, and an overall length is about 1500 mm, for instance.

The marker 334 is used in order that a position of the microcatheter inserted into a living body may be detected from outside by contrastradiography. As the marker 334 there is used a ring made of material that is not transparent to radioactive rays, X-rays, and the like. Corresponding to the sizes of the outer sheath main body 332, there may be used a platinum ring having an inside diameter of 0.85 mm, an outside diameter of 0.9 mm, and a length in the axial direction of 1.0 mm, which are an example of sizes thereof. The marker 334 is fixed to and mounted on the extremity part of the outer sheath main body 332 by suitable medical adhesive or the like.

Referring again to FIG. 20, an outer sheath extremity part is subsequently formed from heat-shrinkable film (S22). The outer sheath extremity part is a pipe that is mounted on the extremity of the outer sheath main body 332, that has an outside diameter larger than the outer sheath main body 332 has, and that has a space therein for housing the coarse-dense stent provided with superelasticity. The heat-shrinkable film is used on the basis of a result of an experiment for making the outside diameter of the outer sheath extremity part as close as possible to the outside diameter of the outer sheath main body 332.

Figure 22:
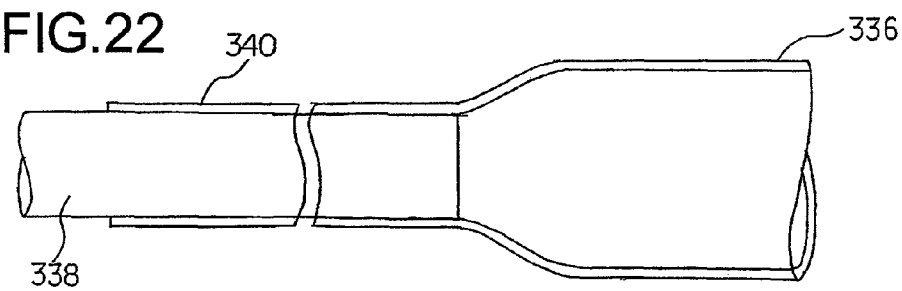
FIG. 22 is a diagram for illustrating a first step of forming the outer sheath main body in the embodiment according to the invention.

The formation of the outer sheath extremity part is carried out through two steps. FIG. 22 is a diagram showing the first step of the formation. In the step, a tube of the heat-shrinkable film with an outside diameter in the order of 2 mm is prepared, the tube put on a molding jig bar 338 having a specified outside diameter in advance, and that portion is heated to a suitable temperature not lower than a heat shrinking temperature. With this operation, an extremity portion of the heat-shrinkable film put on the molding jig bar 338 undergoes heat shrinkage, so that an inside diameter of the portion fits the molding jig bar 338. Preferably, the molding jig bar 338 has been subjected to suitable surface treatment for reducing adhesion to the heat-shrinkable film. Corresponding to the sizes of the outer sheath main body 332, the molding jig bar 338 preferably has the outside diameter of 0.9 mm. A length of the extremity portion of the heat-shrinkable film put on the molding jig bar 338 may be in the order of about 50 mm. Thus the extremity portion having undergone the heat treatment and the heat shrinkage may have an inside diameter of 0.9 mm, an outside diameter of about 1.0 mm, and a length of about 50 mm. The extremity portion corresponds to the outer sheath extremity part 340.

As the heat-shrinkable film it is possible to use FEP (tetrafluoroethylene-hexafluoropropylene copolymer), PTFE (polytetrafluoroethylene) or the like.

Figure 23:
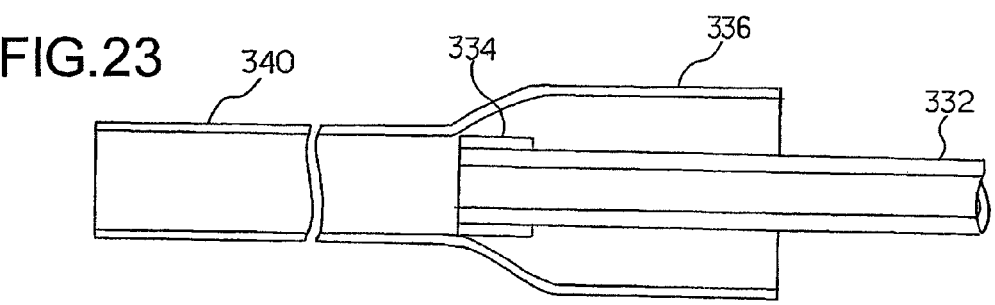
FIG. 23 is a diagram for illustrating a second step of forming the outer sheath main body in the embodiment according to the invention.
Figure 24:
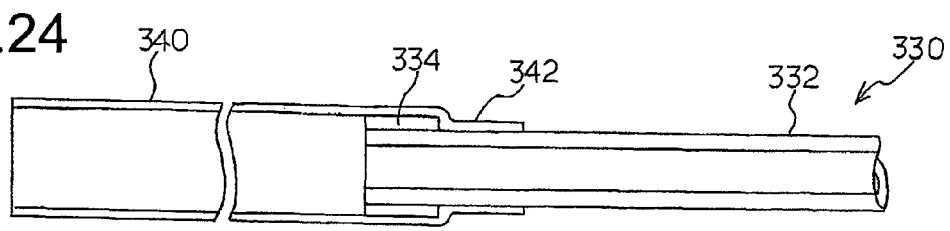
FIG. 24 is a diagram for illustrating an appearance of an outer sheath part in the embodiment according to the invention.

By the first step of the formation, the heat-shrinkable film is obtained having the outer sheath extremity part 340 that is thinned to the outside diameter of 1.0 mm and the inside diameter of 0.9 mm by heat-shrinkage heating, and a root part 336 that has hardly undergone any heat-shrinkage heating and that has the original outside diameter in the order of 2 mm. After the first step of the formation, the second step of the formation is carried out. FIGS. 23 and 24 are diagrams showing the second step of the formation.

As shown in FIG. 23, the outer sheath main body 332 described with reference to FIG. 21 is initially inserted into the root part 336 of the heat-shrinkable film formed in the first step, with the marker 334 positioned on the extremity side. In the above example, in which both the outside diameter of the marker 334 and the inside diameter of the extremity part of the heat-shrinkable film are 0.9 mm, the marker 334 stops just in the vicinity of an entrance of the extremity part of the heat-shrinkable film.

In a state of FIG. 23, subsequently, the root part 336 of the heat-shrinkable film is heated to a suitable temperature not lower than the heat shrinking temperature. The heating may be referred to as secondary heat-shrinkage heating for discrimination from the heat-shrinkage heating in the first step of the formation. This causes heat shrinkage of the root part 336 of the heat-shrinkable film in accordance with external shapes of the marker 334 and the outer sheath main body 332, and the extremity part that has already been thinned by the heat shrinkage in the first step of the formation is thereby fixed firmly to the outer sheath main body 332. A manner of the fixation is shown in FIG. 24. In this manner, there is formed the outer sheath part 330 having the outer sheath extremity part 340 thinned by heat shrinkage and having the length of about 50 mm, and the outer sheath main body 332 having flexibility.

Figure 25:
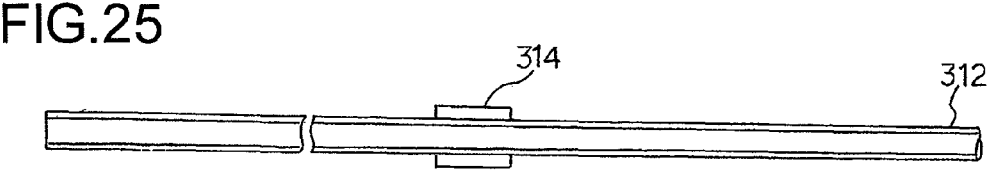
FIG. 25 is a diagram for illustrating an appearance of an inner catheter main body in the embodiment according to the invention.

Referring again to FIG. 20, the insertion of the inner catheter part is subsequently carried out (S26). FIG. 25 is a diagram showing the inner catheter main body 312 and a marker 314 mounted in a position at a distance of about 50 mm from an extremity thereof. The position of the marker 314 corresponds to the length of the outer sheath extremity part 340. The inner catheter main body 312 is a flexible tube having a wire insertion path in which a guide wire 302 that will be described later is inserted and a stent holding part that is provided on an outer circumference on extremity side thereof for holding the coarse-dense stent. The stent holding part corresponds to a portion on extremity side of the marker 314. As the inner catheter main body 312 it is possible to use a stainless tube coated with black resin, for instance, and selected for medical use. In an example of sizes thereof, an outside diameter is 0.43 mm, an inside diameter is 0.25 mm, a tube wall thickness of the tube is 90 μm, and an overall length is about 1600 mm, for instance, which is longer than the overall length of the outer sheath part 330 by a length required for the sliding operation.

The marker 314 has a function similar to that of the marker 334 mounted on the outer sheath main body 332, and a platinum ring is used therefor as a ring made of material not transparent to radioactive rays, X-rays, and the like in order that a position of the catheter main body 312 may be detected from outside by contrastradiography. For achievement of the stop upon contact with the extremity part of the outer sheath main body 332, the marker may have an outside diameter of 0.7 mm, an inside diameter of 0.5 mm, and a length in the axial direction of 1.0 mm, which are an example of sizes thereof. Suitable medical adhesive may be used for the mounting of the marker 314 onto the inner catheter main body 312.

Figure 26:
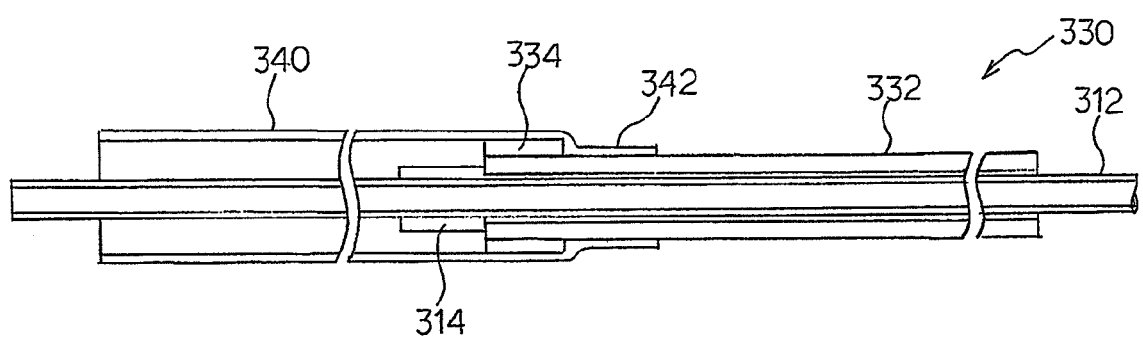
FIG. 26 is a diagram for illustrating a manner of insertion of the inner catheter main body into the outer sheath part in the embodiment according to the invention.

Thus the marker 314 has a function as a stopper when the inner catheter main body 312 is slid in the outer sheath part 330 and is returned to proximal side. FIG. 26 is a diagram showing a state in which the inner catheter main body 312 is inserted into the slide passage in the outer sheath part 330 so that the marker 314 may be stopped by the extremity part of the outer sheath main body 332.

Figure 27:
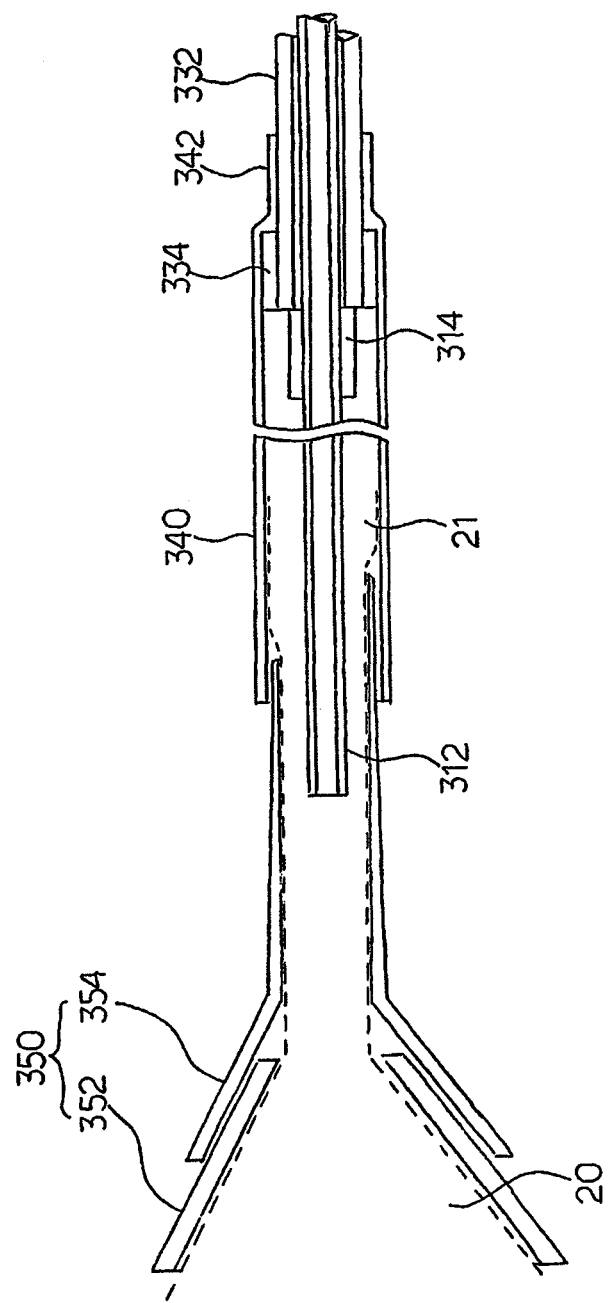
FIG. 27 is a section for illustrating placement of the stent on a stent holding part in the embodiment according to the invention.

Referring again to FIG. 20, integration of the coarse-dense stent provided with superelasticity is carried out (S28). FIGS. 27 and 28 are diagrams illustrating a manner of the integration. As an example of the coarse-dense stent provided with superelasticity, the stent 20 described with reference to FIG. 4 is used therein. The stent 20 is formed so as to be suitable for a blood vessel dilation that exists on a main blood vessel having an inside diameter of about 5 mm and that has an opening with a size D of about 7 mm. In the stent 20 as shown in FIG. 28, having an inside diameter 2R of 5 mm and an overall length of 15 mm in natural length, the thin wire coarsely braided hose portion with LC=3.5 mm, the thin wire densely braided hose portion with LD=8 mm, and the thin wire coarsely braided hose portion with LC=3.5 mm are formed in the stated order along the longitudinal direction thereof. Details of the thin wire coarsely braided hose portions and the thin wire densely braided hose portion are as described with reference to FIG. 4, and application of the thin wire densely braided hose portion on the opening of the blood vessel dilation suppresses blood flow into the blood vessel dilation and suppresses excessive blood flow pressure on the blood vessel dilation.

The stent holding part of the inner catheter main body 312 is an annular space between the outside diameter of the inner catheter main body 312 and the inside diameter of the outer sheath extremity part 340 on an extremity side of the marker 314. In the above example, in which the inside diameter of the outer sheath extremity part 340 is 0.9 mm, the stent 20 is stretched so that the outside diameter thereof of 5 mm in a natural condition is reduced to 0.9 mm, and is placed in the stent holding part. A length of the stretched stent is about 50 mm.

Accordingly, the stent 20 having the outside diameter of 5 mm and the overall length of 15 mm is converted in external shape into an elongated stent 21 having the outside diameter of 0.9 mm and the overall length of 50 mm, which is then inserted into the stent holding part. For the conversion of the stent, it is possible to be use a special jig for shape conversion for stents used for treatment of stenosis of blood vessels or the like, for instance, whereas it is possible to use a two-stage taper insertion jig 350, as shown in FIGS. 27 and 28, with use of flexibility of the stent produced by the braiding of the thin wires.

The two-stage taper insertion jig 350 is composed of a first-stage tapered tube 352 and a second-stage tapered tube 354 mounted on an extremity of the first-stage tube and having an extremity with a diameter smaller than 0.9 mm. A size of a wider opening of the first-stage tapered tube 352 is larger than the outside diameter of 5 mm of the stent 20 on the natural condition. The extremity part of the second-stage tapered tube 354 is sufficiently thin to be inserted into an inside diameter part of the outer sheath extremity part 340 and has an opening cut obliquely. The extremity part of the first-stage tapered tube 352 and the wider opening of the second-stage tapered tube 354 are sized so as to fit each other.

As the first-stage tapered tube 352, it is possible to use a plastic tube having an extremity part thereof softened by heating, thinned by elongation, and cut at a suitable portion. The extremity part of the second-stage tapered tube 354 is so thin that it is difficult to produce the tube by common working of a plastic tube. Herein a thin heat-shrinkable tube having an extremity part shrunken and cut obliquely at a suitable portion is used. The extremity opening cut obliquely is made large enough to allow the outside diameter of the inner catheter main body 312 to be inserted therein and is made smaller than the inside diameter of the outer sheath extremity part 340.

When the stent 20 having the outside diameter of 5 mm is pushed and inserted into the wider opening of the first-stage tapered tube 352 using the two-stage taper insertion jig 350 as shown in FIGS. 27 and 28, the elongated stent 21 stretched so as to have the outside diameter smaller than 0.9 mm comes out of the obliquely cut extremity opening of the second-stage tapered tube 354. Then the two-stage taper insertion jig 350 is positioned so as to be inserted into the inside diameter of the outer sheath extremity part 340 while an extremity part of the inner catheter main body 312 is passed through the obliquely cut extremity opening. The stent 20 having the outside diameter of 5 mm is pushed and inserted into the wider opening of the first-stage tapered tube 352 as described above, so that the elongated stent 21 coming out of the obliquely cut extremity opening of the second-stage tapered tube 354 can be placed in the stent holding part.

With the coarse-dense stent made into the elongated stent 21 and placed in the stent holding part that is the annular space between the outside diameter of the inner catheter main body 312 and the inside diameter of the outer sheath extremity part 340 on the extremity side of the marker 314, a marker 316 is mounted on the extremity part of the inner catheter main body 312. The marker 316 having the same size and made of the same material as the marker 314 may be used therein, and the same adhesive may be used for the mounting thereof onto the inner catheter main body 312. A manner of the mounting is shown in FIG. 29.

The marker 316 is intended to make it possible to know a position of the inner catheter main body 312 from the outside, in the same manner as the marker 314 described with reference to FIG. 25, and further has a function of positioning of the elongated stent 21. Namely, the elongated stent 21 is placed between the marker 316 and the marker 314 described above. With the marker 316 mounted on the inner catheter main body 312, some variation in length of the elongated stent 21 is absorbed by elasticity of the elongated stent 21 in the axial direction, so that the elongated stent is placed over a whole length between the marker 314 and the marker 316.

Referring again to FIG. 20, the coarse-dense stent is thus placed in the stent holding part, and an arrowhead part is subsequently mounted (S30). A manner of the mounting is shown in FIG. 30. The arrowhead part 318 is mounted on the extremity part of the inner catheter main body 312 and is rounded so as not to injure vessels of a living body when the microcatheter is inserted into the living body vessels. A largest outside diameter of the arrowhead part 318 is generally as large as the outside diameter of 1.0 mm of the outer sheath extremity part 340. For the arrowhead part 318 it is possible to use material, such as suitable medical plastic, machined into a desired shape.

In this manner, the markers 314, 316, the elongated state 21, and the arrowhead part 318 are placed on the inner catheter main body 312 so that the inner catheter part 310 is formed.

Referring again to FIG. 20, the guide wire is inserted into the outer sheath part 330 in which the inner catheter part 310 has already been inserted, so that the microcatheter is formed (S32). FIG. 30 shows a state of the microcatheter 300 in which the guide wire 302 is pierced through the inner catheter main body 312 and is protruded from the arrowhead part 318. The guide wire 302 is a flexible thin wire having a function of guiding insertion of the microcatheter 300 into living body vessels. As material of the wire metal or the like suitable for medical use is used. Regarding sizes thereof, a diameter is 0.35 mm and a length is about 1700 mm, which is larger than the length of the inner catheter main body 312.

FIGS. 31 and 32 are diagrams for illustrating functions of the microcatheter 300 formed in the above manner. The inner catheter part 310 and the outer sheath part 330 can be moved relative to each other in the axial direction. Herein, description will be given on the assumption that the outer sheath part 330 is slid with a position of the inner catheter part 310 fixed.

FIG. 31 is a diagram showing a return mode in which the outer sheath part 330 is moved toward the extremity part, in other words, the inner catheter part 310 is slid and returned to the front side relative to the outer sheath part 330. In this mode, the marker 314 of the inner catheter part 310 is at a standstill in contact with the extremity part of the outer sheath main body 332. Then the elongated stent 21 is placed in the stent holding part of the inner catheter part 310, and is housed in the outer sheath extremity part 340.

The return mode is used when the microcatheter 300 is inserted into living body vessels, e.g., into an artery. Then the guide wire 302 is protruded from the arrowhead part 318 so as to be advanced through the artery, while the markers 334, 314, and 316 are observed using contrastradiography, so as to carry the elongated stent 21 to an objective site, e.g., a site having an aneurysm.

Upon advancement to the objective site having the aneurysm, positions of the markers 314 and 316 in front and at rear of the elongated stent 21 are observed, and positioning of the microcatheter 300 is carried out so that the aneurysm comes precisely to a midpoint between the two markers 314 and 316. At that position, the outer sheath part 330 is moved toward the front side, i.e., toward the root part, in other words, the inner catheter part 310 is pushed toward the extremity side relative to the outer sheath part 330. This mode is a push-in mode.

FIG. 32 is a diagram illustrating a manner of the push-in mode. In this mode, the stent holding part protrudes from the outer sheath extremity part 340 to outside, and thus the elongated stent 21 becomes the stent 20 returned to the original state because of becoming free from the outer sheath extremity part 340 having restrained the external shape of the stent. That is, the stent expands in size in the radial directions from 0.9 mm to 5 mm, and returns in size in the longitudinal direction from 50 mm to 15 mm. The position of the stent on that occasion is at the center of the stent holding part and thus the stent 20 expanded and returned to the original shape is placed just on the aneurysm. After that, the microcatheter 300 is drawn through a cylindrical hollow part of the stent 20, so that the stent 20 is left on the aneurysm. The stent 20 has the thin wire densely braided hose portion at the center thereof, this portion blocking the opening of the aneurysm so as to suppress inflow of blood into the aneurysm and resultant increase in blood flow pressure in the aneurysm. The provision of the thin wire coarsely braided hose portions on both sides of the thin wire densely braided hose portion keeps blood flow to collateral vessels on the artery from being blocked.

In this manner, the coarse-dense stent, which is to be left on an objective site such as aneurysm, has a diameter generally as large as or moderately larger than a vessel diameter of an artery, and does not have such a large expanding force that a stent for treatment of stenosis forcibly expands a site of stenosis. Therefore, the outer sheath extremity part 340 covering the circumference of the stent holding part can be a tube obtained from heat shrinkage of the heat-shrinkable film and having a small film thickness, and the outside diameter of the microcatheter 300 can be as small as 1 mm.

INDUSTRIAL APPLICABILITY

As seen from the above description, the stent according to the invention has a configuration that can be placed in a blood vessel and that is capable of closing at least part of an opening of blood vessel dilation such as aneurysma and varix, blocking blood from flowing into the dilation, and thereby preventing the dilation from rupturing, so that the stent can be used as a stent for treatment against blood vessel dilation such as aneurysma and varix, a stent for support of treatment, or a stent for preventing rupture of a blood vessel dilation.

The invention claimed is:

1. A stent, comprising:
a hoselike body braided with a specified length from a plurality of thin wires of superelastic metal, of which, alternately, one-half are wound in a shape of helices in one direction around a cylinder, and the other half are wound in a shape of helices in the other direction, with the thin wires in the one direction and the thin wires in the other direction obliquely intersecting like a plain weave, wherein:
a longitudinally intermediate portion of the hoselike body is formed into a thin wire densely braided hose portion in which mutually neighboring superelastic metal thin wires are in contact with each other or close to each other with a minute interspace, and which has a length required for closure of an opening of blood vessel dilation, wherein both side portions thereof are formed into thin wire coarsely braided hose portions in which mutually neighboring superelastic metal thin wires are provided with diamond-shaped reticulated gaps allowing passage of blood flow with change in size of the reticulated gaps along a longitudinal direction of the hoselike body, while being constant in size thereof along a circumferential direction of the hoselike body such that the size of the reticulated gap of the thin wire coarsely braided hose portions along the circumferential direction of the hoselike body is equal to the size of the reticulated gap of the thin wire densely braided hose portions along the circumferential direction of the hoselike body, by changing intervals in a braiding direction of the plurality of thin wires being same in number as those of the thin wire densely braided hose portion, and
wherein the hoselike body is capable of causing the individual superelastic metal thin wires to extend and finely gather when pulled in a longitudinal direction and allowing resilient restoration to the original hoselike body when released from pulling.

2. A stent provided with superelasticity and having a plurality of thin wires which are composed of shape memory material, of which, alternately, one-half are wound in a shape of helices in one direction around a cylinder, and the other half are wound in a shape of helices in the other direction, with the thin wires in the one direction and the thin wires in the other direction obliquely intersecting like a plain weave, and which are braided into a hoselike body in a longitudinal direction with formation of reticulated gaps in the shape of diamonds, and which is provided with superelasticity, the stent comprising:
thin wire coarsely braided hose portions in which the reticulated gaps having large opening areas are formed with coarse braiding along the longitudinal direction of the hoselike body, and
a thin wire densely braided hose portion in which the reticulated gaps having smaller opening areas are formed with denser braiding than those of the thin wire coarsely braided hose portions with change in size of the reticulated gaps along a longitudinal direction of the hoselike body, while being constant in size thereof along a circumferential direction of the hoselike body such that the size of the reticulated gap of the thin wire coarsely braided hose portions along the circumferential direction of the hoselike body is equal to the size of the reticulated gap of the thin wire densely braided hose portions along the circumferential direction of the hoselike body, by changing intervals in a braiding direction of the plurality of thin wires being same in number as those of the thin wire densely braided hose portion, wherein the narrower of intervals of two intersecting axes in the diamond-shaped reticulated gaps of the thin wire densely braided hose portion is not larger than 0.1 mm.

3. A stent provided with superelasticity and having a plurality of thin wires which are composed of shape memory material, of which, alternately, one-half are wound in a shape of helices in one direction around a cylinder, and the other half are wound in a shape of helices in the other direction, with the thin wires in the one direction and the thin wires in the other direction obliquely intersecting like a plain weave, and which are braided into a hoselike body in a longitudinal direction with formation of reticulated gaps in the shape of diamonds and which is provided with superelasticity, the stent comprising:

thin wire coarsely braided hose portions in which the reticulated gaps having large opening areas are formed with coarse braiding along the longitudinal direction of the hoselike body, and a thin wire densely braided hose portion in which the reticulated gaps having smaller opening areas are formed with denser braiding than those of the thin wire coarsely braided hose portion with change in size of the reticulated gaps along a longitudinal direction of the hoselike body, while being constant in size thereof along a circumferential direction of the hoselike body such that the size of the reticulated gap of the thin wire coarsely braided hose portions along the circumferential direction of the hoselike body is equal to the size of the reticulated gap of the thin wire densely braided hose portions along the circumferential direction of the hoselike body, by changing intervals in a braiding direction of the plurality of thin wires being same in number as those of the thin wire densely braided hose portion, wherein:

the thin wire densely braided hose portion is placed in an intermediate position excluding end portions of an overall length L of the hoselike body in the longitudinal direction, has a length along the longitudinal direction of the hoselike body in a range from one-quarter to one-tenth of the length L, and has the reticulated gaps with the narrower of intervals of two intersecting axes in the diamond-shaped reticulated gaps of not larger than 0.1 mm, and wherein the thin wire coarsely braided hose portions are placed on both sides of the thin wire densely braided hose portion along the longitudinal direction of the hoselike body and have the reticulated gaps with the narrower of intervals of two intersecting axes in the diamond-shaped reticulated gaps being wider than a diameter of a catheter used for treatment of blood vessel dilation.

4. The stent as claimed in claim 3, wherein the thin wire coarsely braided hose portions have the reticulated gaps with the narrower of the intervals of the intersecting two axes in the diamond-shaped reticulated gaps being at least not smaller than 0.6 mm.

5. The stent as claimed in any one of claims 1 through 4, further comprising, thin wire densely braided end portions that are placed at both ends of the hoselike body in the longitudinal direction and that are braided in a denser manner than that for the thin wire coarsely braided hose portions.

\* \* \* \* \*